United States Patent
Reardan et al.

(10) Patent No.: US 11,311,503 B1
(45) Date of Patent: Apr. 26, 2022

(54) STERILE AQUEOUS CHOLINE SALT COMPOSITIONS

(71) Applicant: Protara Therapeutics, Inc., New York, NY (US)

(72) Inventors: Dayton Reardan, Shorewood, MN (US); Jacqueline Zummo, Brooklyn, NY (US)

(73) Assignee: PROTARA THERAPEUTICS, INC., New York, NY (US)

( * ) Notice: Subject to any disclaimer, the term of this patent is extended or adjusted under 35 U.S.C. 154(b) by 0 days.

(21) Appl. No.: 17/246,438

(22) Filed: Apr. 30, 2021

Related U.S. Application Data

(60) Provisional application No. 63/181,858, filed on Apr. 29, 2021.

(51) Int. Cl.
*A61K 31/14* (2006.01)
*A61J 1/14* (2006.01)
*A61K 9/00* (2006.01)

(52) U.S. Cl.
CPC ............. *A61K 31/14* (2013.01); *A61J 1/1493* (2013.01); *A61K 9/0019* (2013.01)

(58) Field of Classification Search
CPC .............................. A61K 31/14; A61J 1/1493
See application file for complete search history.

(56) References Cited

PUBLICATIONS

Strazhevskaya et al., "Effect of choline on DNA supramolecular complexes of rats and animal survival after γ-irradiation", Radiobiologiya, vol. 28, No. 2, pp. 199-200 (1988) (English Abstract).*

* cited by examiner

*Primary Examiner* — Kevin E Weddington
(74) *Attorney, Agent, or Firm* — Seed IP Law Group LLP

(57) ABSTRACT

Disclosed are sterile aqueous choline salt compositions, their preparation, and methods of use. Also disclosed are methods to treat choline deficiency, intestinal failure associated liver disease (IFALD), and fatty liver disease. Additionally disclosed is a method of synthesis of choline salts.

20 Claims, 4 Drawing Sheets

STERILE AQUEOUS CHOLINE SALT COMPOSITIONS

BACKGROUND

Technical Field

The disclosure herein relates to sterile aqueous choline salt compositions, their preparation, and methods of use, particularly in the context of treating conditions associated with choline deficiency.

Description of the Related Art

Choline is an essential nutrient and common component of a normal diet, typically ingested in the form of phosphatidylcholine found in eggs, meat, nuts, and vegetables (Buchman, *Gastroent.*, 2009, 137:S119-S128). The structure of choline comprises a quaternary amine, which acts as a methyl donor in many metabolic reactions, similar to B-vitamins and folate. Choline is necessary for cell membrane structure (e.g., phospholipids), triglyceride transport via very-low-density lipoprotein (VLDL) synthesis, cholesterol transport in bile, intracellular messaging, brain development and function (e.g., acetylcholine). Choline is essential for cell health and survival: hepatocytes die from apoptosis in choline-deprived medium; increased DNA damage and apoptosis has been observed in lymphocytes in choline-deficient vs normal humans, consistent with increased liver cancer rates in rodents after long-term choline depletion (Shin et al., *J. Cell. Biochem.*, 1997; 64:196-208; and da Costa et al., *Am. J. Clin. Nutr.*, 2006; 84:88-94).

95% of choline in the body is in the form of phosphatidylcholine (PC). PC is the primary lipid of the VLDL particle surface monolayer and the membranes of key secretory bodies (e.g., ER, glolgi, cell membrane). Low PC levels inhibit VLDL packaging and secretion (Vance, J. E., and Vance, D. E., 1985, *Can. J. Biochem. Cell Biol.*, 263, 12, 5898-5909). Exogenous choline is required to maintain adequate PC stores. Multiple PC synthesis pathways exist but only the de novo pathway adequately replenishes PC (Boyer, 2013, *Compr. Physiol.*, 3:3). The de novo pathway to PC is CDP-Choline which requires plasma free choline as the root substrate and is ubiquitous in mammalian tissues (Vance, D. E., 2002, in Biochemistry of Lipids, Lipoproteins, and Membranes (Vance, D. E., and Vance, J. E., eds) pp. 205-232). In addition to the CDP-choline pathway for PC synthesis, the liver has a unique phosphatidylethanolamine methyltransferase (PEMT) activity which provides an alternative pathway for PC synthesis (Noga and Vance D. E., 2003, *J. Biol. Chem.*, 278, 24, 21851-21859). However, PEMT itself is partly reliant on choline as betaine (a metabolite of choline) (Sunden, S., Renduchintala, M., Park, E., Miklasz, S., & Garrow, T., 1997) *Arch. Biochem. Biophys.*, 345, 171-174). Other choline and PC salvage and re-synthesis pathways exist, but can only re-circulate rather than create de novo PC (Boyer, 2013, *Compr. Physiol.*, 3:3).

Choline deficiency resulting in diminished levels of phosphatidylcholine adversely affects multiple hepatobiliary functions and can lead to steatosis, cholestasis, and/or hepatic cell death. Steatosis, or fatty liver, is a broad term that describes the buildup of fats in the liver. Cholestasis is a liver disease that occurs when the flow of bile from the liver is reduced or blocked. When bile flow is altered, it can lead to a buildup of bilirubin. PC comprises approximately 40% of bile's organic matter (Schmitz M G J, Renooij W., *Gastroent.*, 1990, 99:1292-1296). Insufficient PC in bile decreases vesicle/mixed micelle formation with cholesterol, increasing free bile salts (Barrios and Lichtenberger, 2000, *Gastroent.*, 118:1179-1186). Free bile salts exert detergent activity on cholangiocytes, restricting bile flow (De Vree, et al., *Proc. Natl. Acad. Sci. USA*, 1998, 95:282-287). Additionally, choline is an important source for intracellular signaling intermediates (Albright, et al., (2005) *Cell. Physiol. Biochem.*, 15(1-4):59-68). Choline deficiency induces fragmentation of DNA in hepatocytes in culture (Albright, et al., 1996, *FASEBJ*, 10, 510-516). Further, hepatocytes die via apoptosis in choline deficient media.

Choline deficiency results in liver injury in animals and healthy adults. An experimental choline deficient diet caused rapid-onset liver abnormalities (e.g., increased liver fat as shown by MM), which were reversed by a normalized diet (Zeisel, et al., *FASEBJ*, 1991, 5:2093-2098; and Fischer, et al., *Am. J Clin. Nutr.*, 2007, 85:1275-1285). These findings are Consistent with findings in several animal species that choline deficiency causes hepatic steatosis and cirrhosis, skeletal muscle and other organ abnormalities (Patek, et al., *Proc. Soc. Exp. Biol. Med.*, 1975, 148:370-374; and reviewed in Buchman, *Nutr. Clin. Pract.*, 2003, 18:353-358).

Intestinal failure (IF) occurs when gut function is reduced below the minimum necessary for the absorption of macronutrients and/or water and electrolytes, such that intravenous supplementation is required to maintain health and/or growth. Often due to surgical removal of bowel (short bowel syndrome) or diseased nonfunctioning bowel. IF is classified into three types: (T-1) which is transient, usually post-operative, and fully reversible; (T-2) which is due to severe illness and requires parenteral nutrition (PN) for weeks or months; and (T-3) which requires long-term PN for survival. The underlying etiology of T-3 stems from diseases such as cancer, Crohn's disease, vascular disease, AIDS, radiation enteritis, and others (Bakker, H. et al., *Clin. Nutr.*, 1999, 18:135-140). Further, after surviving gastrointestinal (GI) disease, a substantial proportion of PN-dependent IF patients develop progressive liver disease or intestinal failure associated liver disease (IFALD).

Liver disease in PN dependent adults and children has been widely observed for decades. Now termed IFALD, it is the complication in IF patients with the greatest risk of death (Pironi et al., *Clin. Nutr.*, 2012, 31:831-45). 47-65% of adult PN patients have chronic cholestasis (Cavicchi, et al., *Ann. Intern. Med.*, 2000, 132:525-532; and Salvino et al., JPEN, 2006, 30:3, 202-208). 42% of all adult PN patients develop complicated liver disease (i.e., extensive portal fibrosis or cirrhosis, bilirubin ≥3.5 mg/dl for ≥1 month, ascites, portal HTN, hepatic encephalopathy or factor V<50%) and 22% of deaths among PN patients are due to liver disease (Cavicchi, et al., *Ann. Intern. Med.*, 2000, 132:525-532). Pathogenesis is presumed to be multi factorial: PN toxicity (lipids), infectious, nutritional deficiencies including choline deficiency are all implicated in the literature.

Choline deficiency in PN patients is common and linked to liver impairment (Buchman, et al., *Clin. Nutr.*, 1993, 12:33-37; Buchman, *Gastroent.*, 2009, 137:S119-128; Chawla, et al., *Gastroent.*, 1989, 97:1514-20; and Burt et al., *Lancet*, 1980, Sep. 20, 638-9). There are only trace amounts of choline (as emulsifier) in PN products, de novo synthesis and secondary pathways are impaired, choline shortage leads to impaired VLDL fat transport and pathological fat build-up in hpatoxyces, which created toxic bile salt accumulation (Noga, et al., *J. Biol. Chem.*, 2003, 278:21851-21859; Lombardi, et al., *J. Lipid Res.*, 1968, 9:437-446; Yao, et al., *J. Biol. Chem.*, 1988, 263:2998-3004; and De Vree, et al., *Proc. Natl. Acad. Sci. USA*, 1998, 95:282-287). Choline is not included in PN products in sufficient amounts, which has been recognized by The American Society for Parenteral and Enteral Nutrition (ASPEN) as needed, but unavailable as a commercial PN product (Vanek et al., *Nutr. Clin. Pract.*, 2012, 27(4), 440-491).

Intravenous (IV) choline administration for IFALD has shown promise in reducing steatosis (Buchman, et al., *Hepatol.*, 1995, 22:1399-1403). IV choline administration in patients >16 years old requiring >80% PN has shown reversal of steatosis and improved cholestasis (Buchman, et al., *J. Parent. Ent. Nutr.*, 2001, 25:260-268). Further, IV choline administration is well-tolerated in patients (Buchman, et al., *Clin. Pharm. Ther.*, 1994, 55:277-83). Administering a nutrient solution containing a choline salt to a patient parenterally, as a method to inhibit fatty liver disease in a human patient has been described (U.S. Pat. No. 5,567,736).

The Food and Drug Administration (FDA) requires that all injectable drug products be sterilized by terminal sterilization or through aseptic processing methods. Terminal sterilization is the preferred method of sterilization for injectable drug products, and takes place after the drug product has been placed into its primary packaging. Terminal sterilization of drug products that are aqueous solutions may involve heat or irradiation. Selection of an appropriate sterilization method requires an in-depth understanding of the physicochemical properties of the drug substance and the characteristics of the final formulated product.

The gamma irradiation process uses Cobalt 60, which emits gamma rays, measured in units of kiloGrays (kGy), during radioactive decay. High-energy gamma radiation interacts with matter to form ion pairs by ejecting electrons, which leads to free radical formation and excitation. Free-radicals are highly reactive and may participate in several types of reactions including gas liberation, double-bond formation and scission, exchange reactions, electron migration or cross-linking. In microorganisms, damage induced by radiation may result in biological changes that result in cell death. Although breaking the covalent bonds of bacterial DNA is considered the major route of cellular damage, membrane damage also may contribute significantly to reproductive-cell death. In solutions, a molecule may receive energy directly from the incident radiation (the "direct effect") or, in aqueous solutions such as parenterals, by the transfer of energy from the radiolysis products of water (e.g., hydrogen and hydroxyl radicals and the hydrated electron) to the solute molecule (the "indirect effect").

It is necessary to examine each new compound to assess its radiation stability. Furthermore, with a formulated medication, the stability of an individual component may change when irradiated as part of the product (Jacobs G. P., Pharmaceutical Technology, 2007 Supplement, Iss. 2). Aqueous parenteral drug products present additional challenges for sterilization via gamma irradiation than those in solid form due the "indirect effect." For example, the hydroxyl radical is the strongest known oxidizing species and is mainly responsible for radiation-induced damage of solutes in irradiated aqueous solutions (Sharma et al. *Advances in Pharmaceutical Product Development and Research*, 2020, Ch. 21, 789-848).

Accordingly, there is a need for sterile aqueous choline salt compositions, and methods to produce the same, for the treatment of conditions associated with choline deficiency.

BRIEF SUMMARY

The present disclosure provides sterile compositions of choline salts in aqueous media, their preparation, and methods of use. The disclosure further provides methods of treating choline deficiency, intestinal failure associated liver disease (IFALD), and fatty liver disease.

DETAILED DESCRIPTION

Figure 1:
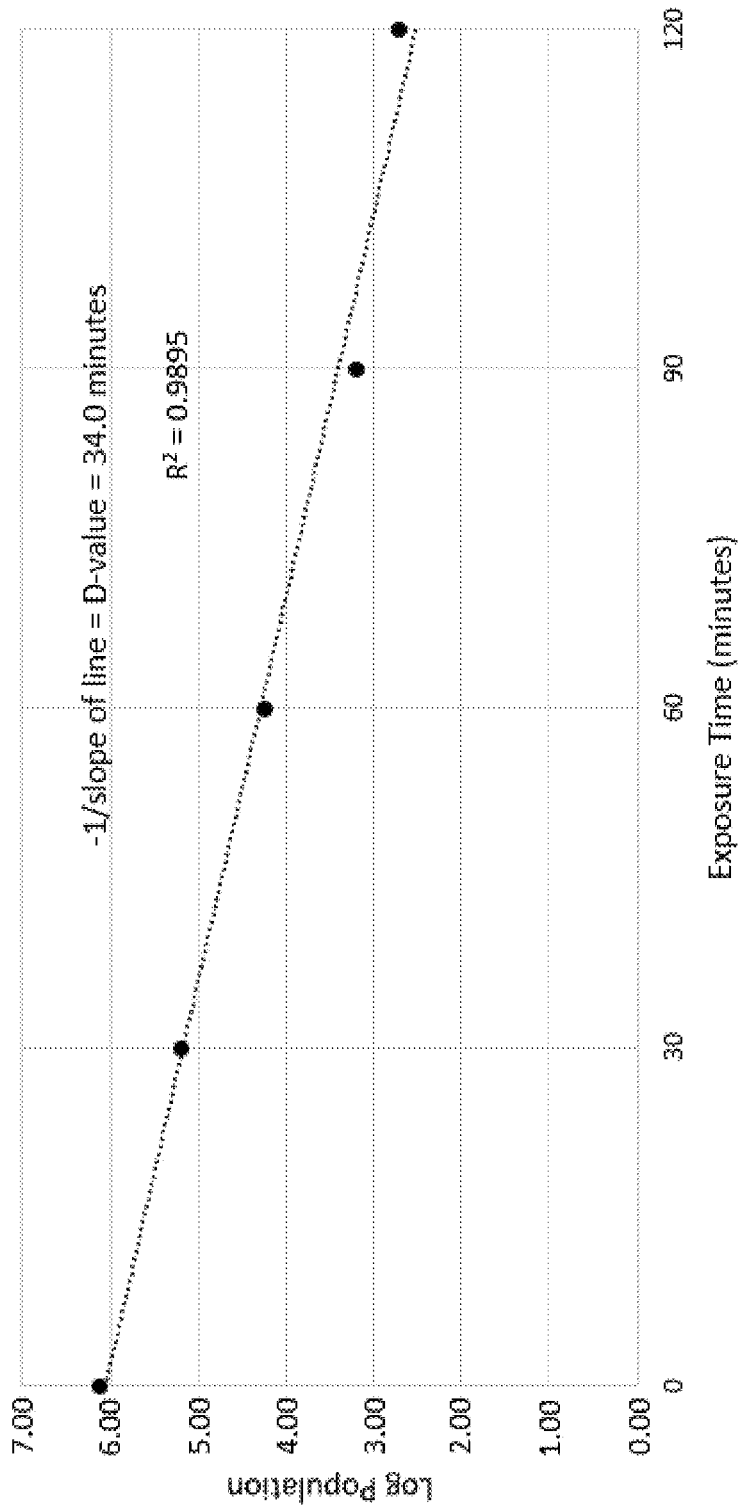
FIG. 1 illustrates a steam survivor curve for *G. stearothermophilus* spores suspended in 50% choline chloride composition ($R^2$=0.9895, −1/slope of line=$D_{121}$-value=34 minutes).

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The term "about" is to be construed as meaning plus or minus 10%. To illustrate, "about 5" means 5±0.5. Terms not specifically defined herein should be given the meanings that would be given to them by one of skill in the art in light of the disclosure and the context.

The terms below, as used herein, have the following meanings, unless indicated otherwise:

"Sterile" is defined as free from viable microorganisms. "Sterilization" is defined as a validated process used to render a product free from viable microorganisms. The presence of microorganisms is expressed as a probability. While the probability can be reduced to a very low number, it can never with certainty be reduced to zero. Therefore, the term "Sterility Assurance Level (SAL)" is used as a measure of sterility. "Sterility Assurance Level (SAL)" refers to the probability of a viable microorganism being present on a product after sterilization, and is normally expressed as $10^{-n}$. SALs can also be used to describe the microbial population that was destroyed by the sterilization process, though this is not the same as the probabilistic definition. What is often called a "log reduction" (technically a reduction by one order of magnitude) represents a 90% reduction in microbial population. Thus a process that achieves a "6-log reduction" ($10^{-6}$) will theoretically reduce an initial population of one million organisms to very close to zero. Sterility may also be expressed by the presence of "Colony Forming Units (CFU)", where CFU is used to describe visible growth of microorganisms arising from a single cell or multiple cells.

"Choline salt" refers to a class of quaternary ammonium salts containing the N,N,N-trimethylethanolammonium cation and corresponding counter anion, which may be represented by the following general formula wherein $X^-$ denotes the corresponding counter anion:

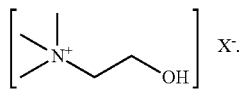

Suitable counter anions include, but are not limited to, halides, such as chloride $Cl^-$, and bitartrate ((2R,3R)-2,3,4-trihydroxy-4-oxobutanoate). Choline salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

"Aqueous media(um)" is defined as a liquid comprising more than about 50% water.

"Weight/volume %" is a way of expressing the concentration of a solution, wherein $$\frac{weight}{volume}\% = \frac{weight\ of\ solute}{volume\ of\ solution} \times 100.$$

"Water for Injection (WFI)" is a sterile, nonpyrogenic preparation of water for injection which contains no bacteriostat, antimicrobial agent, or added buffer.

"Bacteriostat" refers to a substance that prevents the multiplying of bacteria without destroying them.

"Antimicrobial agent" refers to a natural or synthetic substance that kills or inhibits the growth of microorganisms such as bacteria, fungi and algae.

"Preservative" refers to antimicrobial ingredients that are added to compositions to help maintain the safety of the composition by inhibiting the growth of, or reducing the amount of microbial contaminants, or both.

"Amino acid(s)" are simple organic compound containing both a carboxyl (—COOH) and an amino (—NH$_2$) group. The term "amino acid(s)" may refer to naturally occurring or synthetic (i.e., man-made) amino acid(s).

"Vitamin" refers to any of a group of organic compounds which are essential for normal growth and nutrition and are required in small quantities in the diet because they cannot be synthesized by the body. Examples of vitamins may include, but are not limited to, vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

"Fatty acid" refers to a carboxylic acid consisting of a hydrocarbon chain and a terminal carboxyl group, especially any of those occurring as esters in fats and oils. Fatty acids may include, but are not limited to, alpha-linolenic acid, linoleic acid, docosahexaenoic acid, and gamma-linolenic acid.

"Ionic strength" is the total ion concentration in a solution. Ionic strength is calculated by the formula $I=\frac{1}{2}\Sigma_{i=1}^{n} c_i z_i^2$ where, $c_i$ is the molar concentration of ion I (mol/L), $z_i$ is the charge number of that ion, and the sum is taken over all ions in solution. For example, for a 1:1 electrolyte such as choline chloride, where each ion is singly-charged, the ionic strength is equal to the sum of the concentration of each ion (choline$^{+1}$, chloride$^1$).

"Substantially free of microbes, bacteria, or specific strains of bacteria, such as Staphylococcus aureus (S. aureus) or Geobacillus stearothermophilus (G. stearothermophilus)" means having a low (i.e., ≤1 colony-forming unit, CFU/mL) but clinically acceptable level of bacteria. Microbes include viruses, bacteria, archaea, fungi, plants like algae, and protozoa.

"Resistant to microbial growth" means that the composition(s) meet the criteria set forth by, for example, the Food and Drug Administration and the U.S. Pharmacopeia for products made with aqueous bases or vehicles. For example, for bacteria, resistant to microbial growth may mean not less than 1.0 log reduction for the initial calculated count at 7 days, not less than 3.0 log reduction at 14 days, and no increase from the 14 days' count at 28 days. For example, for yeast and molds, resistant to microbial growth may mean no increase from the initial calculated count at 7, 14, and 28 days.

"D-value" or decimal reduction time (or decimal reduction dose) is the time (or dose) required, at a given condition (e.g., temperature) or set of conditions, to achieve a log reduction, that is, to kill 90% (or 1 log or more) of relevant microorganisms.

"Chemically stable" refers to the resistance of a substance to degrade into its known or unknown degradation products. For example, trimethylamine is a known degradation product of choline chloride. The level of trimethylamine that is acceptable can be up to 0.2%.

"Drug product" means a finished dosage form, for example, tablet, capsule, solution, etc., that contains an active drug ingredient generally, but not necessarily, in association with inactive ingredients.

In certain embodiments of the invention, a pH-adjusting agent may be added to the composition. The choice of a pH adjusting agent may affect the resistance to microbial challenge and/or the stability of the choline salt, as measured by the reduction in assayable degradation products. A pH adjusting agent may include acids such as, malic acid, citric acid, acetic acid, boric acid, lactic acid, hydrochloric acid, phosphoric acid, sulfuric acid, sulfonic acid, or nitric acid. A pH adjusting gent may also include bases such as, acetanilide, ammonia, calcium hydroxide, potassium bicarbonate, potassium hydroxide, sodium bicarbonate, sodium dihydrogen phosphate, sodium citrate, sodium taitrate, sodium carbonate, sodium hydroxide, thiourea, or urea. Any pH adjusting agent disclosed herein or as would be known to one of ordinary skill in the art is contemplated herein.

"Pharmaceutical composition" as recited herein is synonymous with composition.

"Pharmaceutically acceptable" refers to molecular entities and compositions that do not produce an adverse, allergic or other untoward reaction when administered to a subject. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Insofar as any conventional media or agent is incompatible with the active ingredient, its use in the therapeutic compositions is not appropriate. Supplementary compatible active ingredients can be incorporated into the compositions. For human administration, preparations should meet sterility, pyrogenicity, general safety and purity standards as required by the Food and Drug Administration (FDA). Conventional procedures and ingredients for the selection and preparation of suitable compositions are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

An "excipient" refers to certain embodiments which are more or less inert substances added as diluents (wherein "diluent" refers to a substance used to dilute something) or vehicles, or to provide form or consistency. Excipients may also enhance resistance to microbial growth, and thus act as a preservative. Such excipients include, but are not limited to, xylitol, mannitol, lactose, starch, magnesium stearate, sodium saccharine, cellulose, cellulose derivatives, magnesium carbonate and the like.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed agent sufficient to achieve a desired effect in a subject will be understood by those of skill in the art in light of this disclosure.

As used herein, the terms "chronic" refers to a medical disorder or condition that persists over time or is frequently recurring.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the treatment. Suitable dosage regimens and/or forms include those set out, for example, in the latest edition of the *Physicians' Desk Reference*, incorporated herein by reference.

"Direct injection" refers to an intravenous injection wherein a substance is injected directly into a vein.

"Indirect injection" refers to an intravenous injection wherein a substance is introduced into another source prior to injection directly into a vein. For example, without limiting possible routes of indirect injection, an indirect injection comprises introducing a substance into an IV bag, wherein the contents of the IV bag are then administered to a subject via injection into a vein as the terminal point of travel (e.g., the contents of the IV bag including, or not including, the substance to be introduced may flow through or be contained in other channels or apparatuses prior to eventual injection into the vein).

A "kit" as used herein, refers to a combination of any number of item(s). For example, a kit may comprise a composition and a syringe for injection of the composition. A kit may also comprise a pre-loaded syringe for injection.

"Gamma irradiation" refers to subjecting a material to gamma radiation, wherein high-energy photons are emitted from an isotope source (e.g., Cobalt 60). High-energy gamma radiation produces electron disruptions (ionization) in any material that it encounters. In living cells, these disruptions result in damage to the DNA and other cellular structures. These photon-induced changes at the molecular level may cause the death of the organism or render the organism incapable of reproduction. This effect is useful in killing bacteria, insects, or other living contaminants, which may exist in, or on, a material.

"Choline deficient" refers to a clinically determined deficiency in choline. Choline is an essential nutrient for humans and is necessary for the normal function of all cells. As a critical component of the cell membrane, it ensures the structural integrity and signaling functions of the cell. Choline is also used for neurotransmission (as the metabolite, acetylcholine), is a major source of methyl donors, and is required for lipid transport from the liver. Considering these many diverse roles, choline deficiency can cause disorders in many bodily systems, including liver, muscle, and lymphocytes in humans and, additionally, the kidney, pancreas, and developing brain and nervous system in animals. Choline deficiency may be characterized as <7 nmol free choline.

"Parenteral nutrition (PN)" refers to intravenous administration of nutrition, which may include protein, carbohydrate, fat, minerals and electrolytes, vitamins and other trace elements for patients who cannot eat or absorb enough food through tube feeding formula or by mouth to maintain good nutrition status.

"Parenteral support" includes administration of parenteral fluids alone or in combination with parenteral nutrition solutions.

"Intestinal failure (IF)" refers to the reduction of gut function below the minimum necessary for the absorption of macronutrients and/or water and electrolytes, such that intravenous supplementation is required to maintain health and/or growth. In some instances, IF may be due to surgical removal of the bowel (short bowel syndrome) or diseased nonfunctioning bowel.

"Intestinal failure associated liver disease (IFALD)" refers to liver disease associated with intestinal failure, which may arise in PN-dependent subjects. In some instances, IFALD develops in patients on long-term parenteral nutrition for chronic intestinal failure, and may be characterized by liver steatosis and/or cholestasis, and may be accompanied by one or more other signs of liver injury including but not limited to, elevated liver function test(s), fibrosis, cirrhosis, and end stage liver disease (ESLD). In some instances, IFALD may previously have been referred to as PN associated liver disease (PNALD).

"Fatty liver disease" refers to a condition characterized by excessive accumulation of lipids (fat) in the liver. The build-up of fat in the liver results in a range of clinical manifestations and progresses in stages. Depending on etiology, each stage can be characterized as non-alcoholic or alcoholic. The progression begins with simple fatty liver, or steatosis. This stage, generally regarded as benign, is characterized by the increased appearance of fat in the liver. Fatty liver can be characterized as non-alcoholic (NAFL) or alcoholic (AFL). The next stage of a fatty liver disease is a form of hepatitis known as steatohepatitis, characterized by further fat accumulation and liver tissue inflammation. Steatohepatitis can be non-alcoholic (NASH) or alcoholic (ASH). Both NASH and ASH can lead to the next stage of fatty liver disease, NASH-associated or ASH-associated fibrosis, respectively, which is characterized by scarring of the liver. Finally, fibrosis can progress to cirrhosis, which causes irreversible damage to the liver and is the most severe stage. Cirrhosis can be non-alcoholic or alcoholic.

"Type 1 glass" refers to a borosilicate glass with good chemical resistance. Type 1 glass is used for pharmaceuticals requiring the least reactive containers. Exemplary products include, but are not limited to, glass vials, filled syringes, cartridges, and ampoules.

"Delamination controlled (DC) glass" refers to glass that is resistant to delamination (i.e., degradation of surface glass). Exemplary products include, but are not limited to, glass vials, filled syringes, cartridges, and ampoules.

"Pure ethanol" refers to 200 proof (100%) ethanol.

"Substantially no(t) detectable" when referring to either 2-chloroethanol or aluminum, refers to an amount of either substance that is within 10% of the limit of detection.

In some embodiments, the present invention provides a sterile composition comprising a choline salt in an aqueous medium.

In certain embodiments, the composition contains 25-75% choline salt by weight/volume %. In specific embodiments, the composition contains 50% choline salt by weight/volume %.

In some embodiments, the choline salt is choline chloride. In other embodiments, the choline salt is choline bitartrate.

In some embodiments, the present invention provides a sterile composition for intravenous injection comprising choline chloride in an aqueous medium, wherein the choline chloride is present in the composition at a level of 25-75% choline chloride salt by weight/volume %.

In some embodiments, the present invention provides a sterile composition for intravenous injection comprising choline chloride in an aqueous medium, wherein the choline chloride is present in the composition at a level of 50% choline chloride salt by weight/volume %.

In some embodiments, the present invention provides a sterile composition for intravenous injection consisting of choline chloride in an aqueous medium, wherein the choline chloride is present in the composition at a level of 50% choline chloride by weight/volume %.

In some embodiments, the aqueous medium is water for injection.

In certain embodiments, the composition does not contain a preservative. In other embodiments, the composition contains a preservative. In some embodiments, the composition contains at least one amino acid, at least one vitamin, and/or at least one fatty acid. In some embodiments, the composition contains at least one amino acid. In still other embodiments, the composition contains at least one vitamin. In certain embodiments, the composition contains at least one fatty acid. In other embodiments, the composition contains a pharmaceutically acceptable carrier, diluent, or excipient.

In some embodiments, the composition has an ionic strength of at least 0.3 Molar. In certain embodiments, the composition has an ionic strength of 0.3-7 Molar. In certain specific embodiments, the composition has an ionic strength of about 7 Molar.

In some embodiments, the composition has a pH of about 4-7.

In some embodiments, the composition is substantially free of microbes. In some embodiments, the composition is substantially free of bacteria.

In some embodiments, the composition is substantially free of S. aureus, G. stearothermophilus, and/or B. pumilus. In certain embodiments, the composition contains less than $10^{-1}$ CFU/mL of S. aureus, G. stearothermophilus, and/or B. pumilus. In certain embodiments, the composition contains less than $10^{-2}$ CFU/mL of S. aureus, G. stearothermophilus, and/or B. pumilus. In certain embodiments, the composition contains less than $10^{-3}$ CFU/mL of S. aureus, G. stearothermophilus, and/or B. pumilus. In certain embodiments, the composition contains less than $10^{-4}$ CFU/mL of S. aureus, G. stearothermophilus, and/or B. pumilus. In certain embodiments, the composition contains less than $10^{-5}$ CFU/mL of S. aureus, G. stearothermophilus, and/or B. pumilus. In certain embodiments, the composition contains less than $10^{-6}$ CFU/mL of S. aureus, G. stearothermophilus, and/or B. pumilus.

In some embodiments, the composition is substantially free of S. aureus. In certain embodiments, the composition contains less than $10^{-1}$ CFU/mL of S. aureus. In certain embodiments, the composition contains less than $10^{-2}$ CFU/mL of S. aureus. In certain embodiments, the composition contains less than $10^{-3}$ CFU/mL of S. aureus. In certain embodiments, the composition contains less than $10^{-4}$ CFU/mL of S. aureus. In certain embodiments, the composition contains less than $10^{-5}$ CFU/mL of S. aureus. In certain embodiments, the composition contains less than $10^{-6}$ CFU/mL of S. aureus.

In some embodiments, the composition is substantially free of G. stearothermophilus. In certain embodiments, the composition contains less than $10^{-1}$ CFU/mL of G. stearothermophilus. In certain embodiments, the composition contains less than $10^{-2}$ CFU/mL of G. stearothermophilus. In certain embodiments, the composition contains less than $10^{-3}$ CFU/mL of G. stearothermophilus. In certain embodiments, the composition contains less than $10^{-4}$ CFU/mL of G. stearothermophilus. In certain embodiments, the composition contains less than $10^{-5}$ CFU/mL of G. stearothermophilus. In certain embodiments, the composition contains less than $10^{-6}$ CFU/mL of G. stearothermophilus.

In some embodiments, the composition is substantially free of B. pumilus. In certain embodiments, the composition contains less than $10^{-1}$ CFU/mL of B. pumilus. In certain embodiments, the composition contains less than $10^{-2}$ CFU/mL of B. pumilus. In certain embodiments, the composition contains less than $10^{-3}$ CFU/mL of B. pumilus. In certain embodiments, the composition contains less than $10^{-4}$ CFU/mL of B. pumilus. In certain embodiments, the composition contains less than $10^{-5}$ CFU/mL of *B. pumilus*. In certain embodiments, the composition contains less than $10^{-6}$ CFU/mL of *B. pumilus*.

In some embodiments, the composition has a sterility assurance level of at least $10^{-3}$ to $10^{-6}$. In certain embodiments, the composition has a sterility assurance level of at least $10^{-3}$. In other embodiments, the composition has a sterility assurance level of at least $10^{-4}$. In other embodiments, the composition has a sterility assurance level of at least $10^{-5}$. In still other embodiments, the composition has a sterility assurance level of at least $10^{-6}$.

In some embodiments, the composition is sterilized by the ionic strength of the composition. In some embodiments, the composition is sterilized by gamma irradiation. In further embodiments, the composition is sterilized by a combination of ionic strength and gamma irradiation. In some embodiments, the gamma irradiation is at least 20 kGy. In some embodiments, the gamma irradiation is 18-25 kGy. In some embodiments, the gamma irradiation is 25-33 kGy. In some embodiments, the gamma irradiation is 45-59 kGy.

In some embodiments, the composition is suitable for administration via indirect injection or via direct injection. In specific embodiments, the composition is suitable for administration via direct injection. In other specific embodiments, the composition is suitable for administered via indirect injection.

In some embodiments, the composition is resistant to microbial growth. In some embodiments, the composition is chemically stable.

In some embodiments, the present invention provides a method of producing a composition comprising combining a choline salt with an aqueous medium, and adjusting the concentration of the choline salt in the aqueous medium.

In some embodiments, the pH is also adjusted. In certain embodiments, the pH adjusting agent is an acid. In specific embodiments, the acid is malic acid, citric acid, acetic acid, boric acid, lactic acid, hydrochloric acid, phosphoric acid, sulfuric acid, sulfonic acid, or nitric acid.

In other embodiments, the pH adjusting agent is a base. In other specific embodiments, the base is acetanilide, ammonia, calcium hydroxide, potassium bicarbonate, potassium hydroxide, sodium bicarbonate, sodium dihydrogen phosphate, sodium citrate, sodium taitrate, sodium carbonate, sodium hydroxide, thiourea, or urea.

In some embodiments, the method comprises sterilizing the composition by the ionic strength of the composition. In some embodiments, the method comprises sterilizing the composition by gamma irradiation. In further embodiments, the method comprises sterilizing the composition by a combination of ionic strength and gamma irradiation.

In some embodiments, the gamma irradiation is at least 20 kGy. In some embodiments, the gamma irradiation is 18-25 kGy. In some embodiments, the gamma irradiation is 25-33 kGy. In some embodiments, the gamma irradiation is 45-59 kGy.

In some embodiments, the present invention provides a method of producing a composition as described herein, comprising combining choline chloride with water for injection to produce a 50% (w/v) solution, that has an ionic strength of about 7M and a pH between about 4-7, and exposing the solution to gamma irradiation to produce a sterility assurance level of at least $10^{-6}$.

In some embodiments, the gamma irradiation is at least 20 kGy. In some embodiments, the gamma irradiation is 18-25 kGy. In some embodiments, the gamma irradiation is 25-33 kGy. In some embodiments, the gamma irradiation is 45-59 kGy.

In some embodiments, the present invention provides a composition as described herein, produced by a method as described herein.

In some embodiments, the present invention provides a composition produced by combining a choline salt and water for injection such that the ionic strength of the composition promotes sterilization of the composition, and further sterilizing the composition by exposure to gamma irradiation. In specific embodiments, the composition contains 50% choline chloride by weight/volume %.

In some embodiments, the composition is filtered through a micron filter. In some embodiments, the composition is filtered through two micron filters in series. In some embodiments, the composition is filtered through a 0.2 micron filter. In some embodiments, the composition is filtered through two 0.2 micron filters in series. In some embodiments, the composition is filtered through a 0.45 micron filter. In some embodiments, the composition is filtered through two 0.45 micron filters in series.

In some embodiments, the present invention provides a method of treating choline deficiency in a subject, comprising administering to the subject an effective amount of a composition as described herein.

In some embodiments, the present invention provides a method of providing parenteral support to a subject, comprising administering to the subject an effective amount of a composition as described herein.

In some embodiments, the present invention provides a method of providing parenteral nutrition to a subject, comprising administering to the subject an effective amount of a composition as described herein.

In some embodiments, the present invention provides a method of treating liver cholestasis in a subject, comprising administering to the subject an effective amount of a composition as described herein.

In some embodiments, the present invention provides a method of treating liver steatosis in a subject, comprising administering to the subject an effective amount of a composition as described herein.

In some embodiments, the present invention provides a method of treating intestinal failure associated liver disease (IFALD) in a subject, comprising administering to the subject an effective amount of a composition as described herein.

In some embodiments, the present invention provides a method of treating a fatty liver disease in a subject, comprising administering to the subject an effective amount of a composition as described herein. In some embodiments, the fatty liver disease is AFL, ASH, NAFL, NASH, NASH-associated liver fibrosis or ASH-associated liver fibrosis. In some embodiments, the fatty liver disease is alcoholic fatty liver (AFL). In some embodiments, the fatty liver disease is alcoholic steatohepatitis (ASH). In some embodiments, the fatty liver disease is non-alcoholic fatty liver (NAFL). In some embodiments, the fatty liver disease is non-alcoholic steatohepatitis (NASH). In some embodiments, the fatty liver disease is NASH-associated liver fibrosis. In some embodiments, the fatty liver disease is ASH-associated liver fibrosis.

In some embodiments, the treatment comprises administering a composition as described herein to a subject as parenteral support. Parenteral support includes administration of parenteral fluids alone or in combination with parenteral nutrition solutions. For example, a solution comprising a composition as described herein may be provided through a Y-line administration as a stand alone when just fluid is administered. In some embodiments, the treatment comprises administering a composition as described herein to a subject as part of a parenteral support solution, wherein administration occurs at least once per day or as determined by the treating physician. In some embodiments, the treatment comprises administering a composition as described herein to a subject as part of a parenteral support solution, wherein administration occurs at least once per day or on a schedule to obtain normal plasma levels of choline as determined by the treating physician. For example, infusion time may be several hours (e.g., 10-14 hours), which may be administered continuously or may be broken up in one or more administration intervals.

In some embodiments, the treatment comprises administering a composition as described herein to a subject as part of a parenteral nutrition solution. In some embodiments, the treatment comprises administering a composition as described herein to a subject as part of a parenteral nutrition solution, wherein administration occurs at least once per day or as determined by the treating physician. In some embodiments, the treatment comprises administering a composition as described herein to a subject as part of a parenteral nutrition solution, wherein administration occurs at least once per day or on a schedule to obtain normal plasma levels of choline as determined by the treating physician. For example, infusion time may be several hours (e.g., 10-14 hours), which may be administered continuously or may be broken up in one or more administration intervals.

In specific embodiments, the composition as described herein, is administered to a subject via direct injection. In other specific embodiments, the composition as described herein, is administered to a subject via indirect injection.

In some embodiments, the present invention provides a choline salt composition, wherein the composition has been sterilized in liquid form by gamma irradiation of at least 25 kGy and is the irradiation product of a composition comprising a 25-75% choline salt by weight/volume % in an aqueous medium, wherein the composition has a: (a) pH of about 4-7; (b) ionic strength >0.3 M; and (c) a sterility assurance level of at least $10^{-3}$ to $10^{-6}$. In specific embodiments, the ionic strength of the composition is about 7M. In specific embodiments, the sterility assurance level of the composition is at least $10^{-6}$ M. In specific embodiments, the aqueous medium is water for injection. In specific embodiments, the choline salt is choline chloride. In specific embodiments, the composition comprises 50% choline salt by weight/volume %.

In some embodiments, the composition is for use in a method of treating choline deficiency in a subject comprising administering to the subject an effective amount of a composition as described herein. In some embodiments, the composition is for use in a method of treating a deficiency in parenteral support in a subject comprising administering to the subject an effective amount of a composition as described herein. In some embodiments, the composition is for use in a method of treating a deficiency in parenteral nutrition in a subject comprising administering to the subject an effective amount of a composition as described herein. In some embodiments, the composition is for use in a method of treating liver steatosis in a subject comprising administering to the subject an effective amount of a composition as described herein. In some embodiments, the composition is for use in a method of treating liver cholestasis in a subject comprising administering to the subject an effective amount of a composition as described herein. In some embodiments, the composition is for use in a method of treating intestinal failure associated liver disease (IFALD) in a subject comprising administering to the subject an effective amount of a composition as described herein. In some embodiments, the composition is for use in a method of treating a fatty liver disease in a subject comprising administering to the subject an effective amount of a composition as described herein. In some embodiments, the fatty liver disease is AFL, ASH, NAFL, NASH, NASH-associated liver fibrosis or ASH-associated liver fibrosis.

In some embodiments, the present invention provides a composition as described herein, wherein the composition is packaged in the form of a vial for injection.

In some embodiments, the composition is packaged in a glass container. In some embodiments, the composition is packaged in a Type 1 glass container. In other embodiments, the composition is packaged in a delamination controlled (DC) glass container.

In some embodiments, the present invention provides a composition as described herein, wherein the composition is packaged in the form of an IV bag.

In some embodiments, the present invention provides a composition as described herein, wherein the composition is packaged in the form of a pre-loaded syringe.

In some embodiments, the present invention provides a composition as described herein, wherein the composition is packaged in the form of a kit comprising the composition and a syringe. In specific embodiments, the kit comprises the composition packaged in a glass container. In specific embodiments, the kit comprises the composition packaged in a Type 1 glass container. In specific embodiments, the kit comprises the composition packaged in a delamination controlled (DC) glass container. In specific embodiments, the kit comprises the composition packaged in an IV bag. In other specific embodiments, the kit comprises the composition packaged as a pre-loaded syringe.

In some embodiments, the present invention provides a composition and packaging as described herein, wherein the composition and packaging are sterilized by gamma irradiation. In some embodiments, the present invention provides a composition and packaging as described herein, wherein the composition is sterilized by both ionic strength and gamma irradiation and the packaging is sterilized by gamma irradiation. In specific embodiments, the composition and packaging are sterilized by gamma irradiation of at least 20 kGy. In some embodiments, the composition and packaging are sterilized by gamma irradiation of 18-25 kGy. In some embodiments, the composition and packaging are sterilized by gamma irradiation of 25-33 kGy. In some embodiments, the composition and packaging are sterilized by the gamma irradiation of 45-59 kGy.

In some embodiments, the present invention provides a sterile, ready to use pharmaceutical composition of choline chloride comprising: a primary packaging container containing a sterile aqueous choline chloride solution having a concentration of 25-75% choline chloride by weight/volume % in an aqueous medium; and a seal sealing the primary packaging container; wherein the choline chloride solution is free of viable microbial contamination in accordance with a sterility assurance level of at least $10^{-3}$ to $10^{-6}$. In specific embodiments, the aqueous choline chloride solution has a concentration of 50% choline chloride by weight/volume %. In specific embodiments, the sterility assurance level is at least $10^{-6}$. In certain embodiments, the aqueous medium is water for injection. In some embodiments, the primary packaging is a glass container. In some embodiments, the primary packaging is a Type 1 glass container. In other embodiments, the primary packaging is a DC glass container. In still other embodiments, the primary packaging is a in an IV bag. In further embodiments, the primary packaging is a pre-loaded syringe.

In some embodiments, the ready to use pharmaceutical composition is sterilized by gamma irradiation. In specific embodiments, ready to use pharmaceutical composition is sterilized by gamma irradiation of at least 20 kGy. In other specific embodiments, ready to use pharmaceutical composition is sterilized by gamma irradiation of 25-33 kGy. In other specific embodiments, ready to use pharmaceutical composition is sterilized by gamma irradiation of 45-59 kGy.

In some embodiments, the ready to use pharmaceutical composition is suitable for administration via indirect injection. In other embodiments, the ready to use pharmaceutical is suitable for administration via direct injection. In further embodiments, the ready to use pharmaceutical is stable in the primary packaging for at least 3 months.

In some embodiments, the present invention provides a sterile aqueous choline chloride drug product produced by the process of: (i) dissolving choline chloride in water for injection to a final concentration of 40-60% choline chloride by weight/volume %; (ii) filtering the solution through a micron filter; (iii) transferring the solution to a glass vial; (iv) sealing the vial; (v) sterilizing the drug product using gamma irradiation. In certain embodiments, in step (ii) the sterile aqueous choline chloride drug product is filtered through a 0.2 micron filter. In certain embodiments, in step (ii) the sterile aqueous choline chloride drug product is filtered through a 0.45 micron filter. In certain embodiments, in step (ii) the sterile aqueous choline chloride drug product is filtered through two micron filters in series.

In some embodiments, the present invention provides a sterile aqueous choline chloride drug product produced by the process of: (i) dissolving choline chloride in water for injection to a final concentration of 40-60% choline chloride by weight/volume %; (ii) filtering the solution through a 0.2 micron filter; (iii) transferring the solution to a glass vial; (iv) sealing the vial; (v) sterilizing the drug product using gamma irradiation.

In specific embodiments, the sterile aqueous choline chloride drug product contains 50% choline chloride by weight/volume %. In certain embodiments, the sterile aqueous choline chloride drug product is filtered through two 0.2 micron filters in series. In certain embodiments, the sterile aqueous choline chloride drug product is filtered through two 0.45 micron filters in series. In further embodiments, the sterile aqueous choline chloride drug product is sterilized by gamma irradiation of at least 20 kGy. In further specific embodiments, the sterile aqueous choline chloride drug product is sterilized by gamma irradiation of 25-33 kGy. In further specific embodiments, the sterile aqueous choline chloride drug product is sterilized by gamma irradiation of 45-59 kGy.

In some embodiments, the sterile aqueous choline chloride drug product is transferred to a vial, wherein the vial is a glass container. In some embodiments, the sterile aqueous choline chloride drug product is transferred to a vial, wherein the vial is a Type 1 glass container. In some embodiments, the sterile aqueous choline chloride drug product is transferred to a vial, wherein the vial is a DC glass container. In specific embodiments, the sterile aqueous choline chloride drug product is sealed in a vial, wherein the vial is sealed with a rubber stopper. In further specific embodiments, the sterile aqueous choline chloride drug product is sealed in a vial, wherein the vial is further sealed with an aluminum crimp.

In certain embodiments, the drug product does not contain a preservative. In other embodiments, the drug product contains a preservative. In some embodiments, the drug product contains at least one amino acid, at least one vitamin, and/or at least one fatty acid. In some embodiments, the drug product contains at least one amino acid. In still other embodiments, the drug product contains at least one vitamin. In certain embodiments, the drug product contains at least one fatty acid. In other embodiments, the drug product contains a pharmaceutically acceptable carrier, diluent, or excipient.

In some embodiments, the drug product has an ionic strength of at least 0.3 Molar. In certain embodiments, the drug product has an ionic strength of 0.3-7 Molar. In certain specific embodiments, the drug product has an ionic strength of about 7 Molar.

In some embodiments, the drug product has a pH of about 4-7.

In some embodiments, the drug product is substantially free of microbes. In some embodiments, the drug product is substantially free of bacteria.

In some embodiments, the drug product is substantially free of S. aureus, G. stearothermophilus, and/or B. pumilus. In certain embodiments, the drug product contains less than $10^{-1}$ CFU/mL of S. aureus, G. stearothermophilus, and/or B. pumilus. In certain embodiments, the drug product contains less than $10^{-2}$ CFU/mL of S. aureus, G. stearothermophilus, and/or B. pumilus. In certain embodiments, the drug product contains less than $10^{-3}$ CFU/mL of S. aureus, G. stearothermophilus, and/or B. pumilus. In certain embodiments, the drug product contains less than $10^{-4}$ CFU/mL of S. aureus, G. stearothermophilus, and/or B. pumilus. In certain embodiments, the drug product contains less than $10^{-5}$ CFU/mL of S. aureus, G. stearothermophilus, and/or B. pumilus. In certain embodiments, the drug product contains less than $10^{-6}$ CFU/mL of S. aureus, G. stearothermophilus, and/or B. pumilus.

In some embodiments, the drug product is substantially free of S. aureus. In certain embodiments, the drug product contains less than $10^{-1}$ CFU/mL of S. aureus. In certain embodiments, the drug product contains less than $10^{-2}$ CFU/mL of S. aureus. In certain embodiments, the drug product contains less than $10^{-3}$ CFU/mL of S. aureus. In certain embodiments, the drug product contains less than $10^{-4}$ CFU/mL of S. aureus. In certain embodiments, the drug product contains less than $10^{-5}$ CFU/mL of S. aureus. In certain embodiments, the drug product contains less than $10^{-6}$ CFU/mL of S. aureus.

In some embodiments, the drug product is substantially free of G. stearothermophilus. In certain embodiments, the drug product contains less than $10^{-1}$ CFU/mL of G. stearothermophilus. In certain embodiments, the drug product contains less than $10^{-2}$ CFU/mL of G. stearothermophilus. In certain embodiments, the drug product contains less than $10^{-3}$ CFU/mL of G. stearothermophilus. In certain embodiments, the drug product contains less than $10^{-4}$ CFU/mL of G. stearothermophilus. In certain embodiments, the drug product contains less than $10^{-5}$ CFU/mL of G. stearothermophilus. In certain embodiments, the drug product contains less than $10^{-6}$ CFU/mL of G. stearothermophilus.

In some embodiments, the drug product is substantially free of B. pumilus. In certain embodiments, the drug product contains less than $10^{-1}$ CFU/mL of B. pumilus. In certain embodiments, the drug product contains less than $10^{-2}$ CFU/mL of B. pumilus. In certain embodiments, the drug product contains less than $10^{-3}$ CFU/mL of B. pumilus. In certain embodiments, the drug product contains less than $10^{-4}$ CFU/mL of *B. pumilus*. In certain embodiments, the drug product contains less than $10^{-5}$ CFU/mL of *B. pumilus*. In certain embodiments, the drug product contains less than $10^{-6}$ CFU/mL of *B. pumilus*.

In some embodiments, the drug product has a sterility assurance level of at least $10^{-3}$ to $10^{-6}$. In certain embodiments, the drug product has a sterility assurance level of at least $10^{-3}$. In other embodiments, the drug product has a sterility assurance level of at least $10^{-4}$. In other embodiments, the drug product has a sterility assurance level of at least $10^{-5}$. In still other embodiments, the drug product has a sterility assurance level of at least $10^{-6}$.

In some embodiments, the drug product is resistant to microbial growth. In some embodiments, the drug product is chemically stable.

In specific embodiments, the drug product as described herein, is administered to a subject via direct injection. In other specific embodiments, the drug product as described herein, is administered to a subject via indirect injection.

In some embodiments, the present invention provides a drug product as described herein, wherein the drug product is packaged in the form of a kit comprising the drug product and a syringe.

In some embodiments, the present invention provides a drug product and packaging as described herein, wherein the drug product and packaging are sterilized by gamma irradiation. In some embodiments, the present invention provides a drug product and packaging as described herein, wherein the drug product is sterilized by both ionic strength and gamma irradiation and the packaging is sterilized by gamma irradiation. In specific embodiments, the drug product and packaging are sterilized by gamma irradiation of at least 20 kGy. In some embodiments, the drug product and packaging are sterilized by gamma irradiation of 18-25 kGy. In some embodiments, the drug product and packaging are sterilized by gamma irradiation of 25-33 kGy. In some embodiments, the drug product and packaging are sterilized by the gamma irradiation of 45-59 kGy.

In some embodiments, the present invention provides a method of treating choline deficiency in a subject, comprising administering to the subject an effective amount of a drug product as described herein.

In some embodiments, the present invention provides a method of providing parenteral support to a subject, comprising administering to the subject an effective amount of a drug product as described herein.

In some embodiments, the present invention provides a method of providing parenteral nutrition to a subject, comprising administering to the subject an effective amount of a drug product as described herein.

In some embodiments, the present invention provides a method of treating liver cholestasis in a subject, comprising administering to the subject an effective amount of a drug product as described herein.

In some embodiments, the present invention provides a method of treating liver steatosis in a subject, comprising administering to the subject an effective amount of a drug product as described herein.

In some embodiments, the present invention provides a method of treating intestinal failure associated liver disease (IFALD) in a subject, comprising administering to the subject an effective amount of a drug product as described herein.

In some embodiments, the present invention provides a method of treating a fatty liver disease in a subject, comprising administering to the subject an effective amount of a drug product as described herein. In some embodiments, the fatty liver disease is AFL, ASH, NAFL, NASH, NASH-associated liver fibrosis or ASH-associated liver fibrosis. In some embodiments, the fatty liver disease is alcoholic fatty liver (AFL). In some embodiments, the fatty liver disease is alcoholic steatohepatitis (ASH). In some embodiments, the fatty liver disease is non-alcoholic fatty liver (NAFL). In some embodiments, the fatty liver disease is non-alcoholic steatohepatitis (NASH). In some embodiments, the fatty liver disease is NASH-associated liver fibrosis. In some embodiments, the fatty liver disease is ASH-associated liver fibrosis.

In some embodiments, the present invention provides a method for treating choline deficiency in a subject, comprising administering to the subject an effective amount of a composition or drug product as described herein. In some embodiments, the present invention provides a method for treating choline deficiency in a subject, comprising administering to the subject an effective amount of a composition as described herein. In some embodiments, the present invention provides a method for treating choline deficiency in a subject, comprising administering to the subject an effective amount of a drug product as described herein.

In some embodiments, the method for treating choline deficiency in a subject further comprises providing parenteral support or parenteral nutrition to the subject. In some embodiments, the method for treating choline deficiency in a subject further comprises providing parenteral support to the subject. In some embodiments, the method for treating choline deficiency in a subject further comprises providing parenteral nutrition to a subject.

In some embodiments, the choline deficiency in a subject is associated with liver cholestasis or liver steatosis. In some embodiments, the choline deficiency in a subject is associated with liver cholestasis. In some embodiments, the choline deficiency in a subject is associated with liver steatosis. In some embodiments, the choline deficiency in a subject is associated with intestinal failure associated liver disease (IFALD). In some embodiments, the choline deficiency in a subject is associated with a fatty liver disease. In some embodiments, the choline deficiency in a subject is associated with a fatty liver disease, wherein the fatty liver disease is AFL, ASH, NAFL, NASH, NASH-associated liver fibrosis or ASH-associated liver fibrosis. In some embodiments, the choline deficiency in a subject is associated with a fatty liver disease, wherein the fatty liver disease is AFL. In some embodiments, the choline deficiency in a subject is associated with a fatty liver disease, wherein the fatty liver disease is ASH. In some embodiments, the choline deficiency in a subject is associated with a fatty liver disease, wherein the fatty liver disease is NAFL. In some embodiments, the choline deficiency in a subject is associated with a fatty liver disease, wherein the fatty liver disease is NASH. In some embodiments, the choline deficiency in a subject is associated with a fatty liver disease, wherein the fatty liver disease is NASH-associated liver fibrosis. In some embodiments, the choline deficiency in a subject is associated with a fatty liver disease, wherein the fatty liver disease is ASH-associated liver fibrosis.

In some embodiments, the present invention provides a method of synthesizing choline chloride comprising introducing gaseous trimethylamine into a hydrogenator, under pressure, with 2-chloroethanol, in the presence of pure ethanol and methyl-tert-butyl ether, wherein the process is a non-continuous process.

In some embodiments, the choline chloride is produced in >99% purity. In some embodiments, the choline chloride is produced in >99.5% purity. In some embodiments, the choline chloride is produced in >99.8% purity.

In some embodiments, the choline chloride is produced with substantially no detectable 2-chloroethanol. In some embodiments, the choline chloride is produced with substantially no detectable aluminum. In some embodiments, the choline chloride is produced with ≤0.05 ug/g of aluminum. In some embodiments, the choline chloride is produced with ≤0.1% wt:wt of trimethylamine.

Abbreviations

The following abbreviations are used in the examples, while other abbreviations have their customary meaning in the art:
MTBE: methyl tert-butyl ether
WFI: water for injection
g: gram
L: liter
mL: milliliter
mol: mole
min: minutes
h or hr: hour(s)
M: mol/L or "molar"
° C.: degrees Celsius
CFU: colony forming unit
TNTC: too numerous to count
kGy: kilo Gray
USP: United States Pharmacopeia
RH: relative humidity
VLDL: very-low-density lipoprotein
PC: phosphatidylcholine
PEMT: phosphatidylethanolamine methyltransferase
DNA: deoxyribonucleic acid
MM: magnetic resonance imaging
IF: intestinal failure
PN: parenteral nutrition
IFALD: intestinal failure associated liver disease
IV: intravenous
ESLD: end stage liver disease
PNALD: PN associated liver disease
NAFL: non-alcoholic fatty liver
AFL: alcoholic fatty liver
NASH: non-alcoholic steatohepatitis
ASH: alcoholic steatohepatitis
DC: delamination controlled
TSB: tryptic soy broth
TSA: tryptic soy agar
NLT: not less than
NMT: not more than
RRT: relative retention time
RH: relative humidity
HIAC: high accuracy
LC: liquid chromatography
TS: terminal sterilization
API: active pharmaceutical ingredient
FTIR: fourier-transform infrared spectroscopy
GC-MS: gas chromatography-mass spectrometry
ICP-MS: inductively coupled plasma mass spectrometry
IC: ion chromatography
QL: quantitation limit

EXAMPLES

Embodiments of the invention are further illustrated by the following examples. The examples below are non-limiting are merely representative of various aspects of embodiments of the invention.

Example 1

Preparation of Choline Salt Compositions

Choline chloride (500 g) is combined with WFI, the choline chloride is dissolved, and the total volume is brought up to 1 L, resulting in a choline chloride 50% (w/v) in WFI.

Example 2

Sterilization of Choline Salt Compositions by Ionic Strength

Most single celled organisms maintain a normal ionic strength inside their cell of about 0.3 M. Bacteria in any medium that is higher than 0.3 M in ionic strength will pull water from inside the bacteria until both the inside and outside are equal. Bacteria cannot survive normally with little to no water inside their cell membrane. Thus, ionic strength may be used as a method of reducing the population of bacteria in a medium, thereby sterilizing that medium. Here, the ionic strength of the choline chloride 50% (w/v) in WFI is approximately 7M, which likely imparts bactericidal effects. However, the ionic strength of choline chloride 50% (w/v) in WFI is not sufficient to sterilize against organisms such as *G. stearothermophilus*, *B. pumilus*, and *S. aureous*. Thus, other methods of sterilization such as heat and gamma irradiation were investigated.

Example 3

Sterilization of Choline Salt Compositions by Heat

The $D_{121}$-value was determined for *G. stearothermophilus* spores suspended in a 50% choline chloride composition. Vials containing choline chloride 50% (w/v) in WFI were inoculated with $10^6$ spores of *G. stearothermophilus* per vial and sealed. Microbial assays were performed on the inoculated vials initially (initial population=1.3031×$10^6$ spores) and upon completion of the study (final population=1.1813× $10^6$ spores). These assays verified that the spore concentration in the vials was stable for the duration of the study.

The $D_{121}$-value determination for *G. stearothermophilus* spores suspended in 50% choline chloride composition was determined using spore population data from unexposed vials and vials exposed for 30.0, 60.0, 90.0, and 120.0 minutes. Vials were exposed at 121° C. in a Joslyn/Steris Sterilizer Corp. steam B.I.E.R. Population assays were then performed to determine the spore populations in terms of colony forming units (CFUs). Four replicate units were tested in the same dilution assay at each exposure time. Thus, plate counts listed below are per assay (per four units), while the final population is listed as spores per one unit. Using the spore populations per vial corresponding to each exposure time (see, Table 1, numbers in bold used to calculate final populations with guidance from USP Section 55), a survivor curve was created, and the $D_{121}$-value was calculated according to the Survivor Curve Method (see, FIG. 1).

TABLE 1

CFU Count Data and Population Data for Exposures to Choline Chloride Injection in Vials at 121° C.

| Dilution | Exposure Time (minutes) | | | | | | | | | |
|---|---|---|---|---|---|---|---|---|---|---|
| | 0.0 | | 30.0 | | 60.0 | | 90.0 | | 120.0 | |
| | CFU Count per Plate | | | | | | | | | |
| 2(1/50) | — | --- | — | — | TNTC | TNTC | 232 | 229 | 73 | 87 |
| 1/50 | — | — | TNTC | TNTC | TNTC | TNTC | 138 | 132 | 34 | 21 |
| 1/500 | — | — | TNTC | TNTC | 112 | 162 | 10 | 11 | — | — |
| 1/5,000 | — | — | 97 | 147 | 10 | 11 | — | — | — | — |
| 1/50,000 | 100 | 87 | 5 | 9 | — | — | — | — | — | — |
| ½(1/50,000) | 53 | 62 | — | — | — | — | — | — | — | — |
| Population per Vial | $1.3031 \times 10^6$ | | $1.5250 \times 10^5$ | | $1.7125 \times 10^4$ | | $1.5641 \times 10^3$ | | $5.0000 \times 10^2$ | |

The stability of *G. stearothermophilus* spores suspended in Choline Chloride Injection in vials was demonstrated. The final population was greater than $1.0 \times 10^6$ spores/vial. The $D_{121}$-value of *G. stearothermophilus* spores suspended in choline chloride 50% (w/v) in WFI was found to be 34.0 minutes. A $D_{121}$ value of 34 minutes would result in a sterilization cycle of over 7 hours. A 7-hour sterilization cycle may result in degradation or formation of degradants. As such, terminal sterilization with steam is not feasible.

Example 4

Gamma Irradiation of Choline Salt Compositions

Since sterilization by terminal sterilization is not feasible due to very high $D_{121}$-value (~34 minutes), the feasibility of gamma-irradiation for sterilization of choline salt compositions was evaluated using choline chloride injection, 50(w/v) in WFI. Analytical results of the gamma irradiation feasibility study are summarized in Table 2.

In brief, vials and glassware were heat treated to ensure sterility. The initial pH of Choline Chloride 50% (w/v) in WFI solution was determined. Spiked samples were prepared by inoculation with either *G. stearothermophilus* ($10^6$ spores) or *B. pumilus* ($10^6$ spores). Vials were irradiated at a gamma dose of either 25-33 kGy (kilo Gray) or 45-59 kGy. Control vials were not exposed to gamma irradiation.

TABLE 2

Analytical Results for Gamma Irradiation feasibility

| | Irradiated Samples | | Control sample |
|---|---|---|---|
| Attribute | Gamma dose 25-33 kGy | Gamma dose 45-59 kGy | (non-irradiated) |
| Visual Appearance | Clear, colorless solution free of visible particulates | Clear, colorless solution free of visible particulates | Clear, colorless solution free of visible particulates |
| Assay/Related Substances | Conforms | Conforms | Conforms |
| Assay, % LC | 98.7 | 98.2 | 99.5 |
| TMA (trimethylamine) % | 0.07 | 0.14 | <0.05 |
| Unknown Impurity % | n/a | 0.05 | n/a |
| Total Impurities | 0.07% | 0.19 | <0.05 |
| pH | [1]4.2, [2]4.4 | [1]3.9, [2]4.2 | [1]7.1, [2]6.2 |

[1]neat samples,
[2]1:10 diluted samples

The results in Table 2 indicate that a gamma irradiation dose of 45-59 kGy generates higher impurities (both known and unknown) in the drug product as compared to control. A gamma irradiation dose of 25-33 kGy generates slightly a higher percent of known impurity, triethylamine, in the drug product as compared to control, but it is below identification limit for unknown impurities. Based on these results, it was determined that the optimal range is 25-33 kGy gamma dose for sterilization of choline chloride injection, 50% (w/v) in WFI.

Example 5

Sterilization of Choline Salt Compositions by Gamma Irradiation

I. Gamma sterilization of *G. stearothermophilus/B. pumilus*

Gamma irradiation was tested as a method of sterilization for a composition of choline chloride 50% (w/v) in WFI inoculated with either *Geobacillus stearothermophilus* (*G. stearothermophilus*) or *Bacillus pumilus* (*B. pumilus*). Vials containing the composition were inoculated with 0.1 mL of a *G. stearothermophilus* spore suspension which resulted in a population of $10^6$ CFU per vial. In this manner, separate vials were inoculated with *Bacillus pumilus* (*B. pumilus*). Vials were sterilized using gamma irradiation using either 25-33 kGy or 45-59 kGy. Select vials were left unexposed to be used as positive controls (see, Table 4). All vials were then assayed to determine the spore populations in terms of CFUs (see, Table 3). Additional vials were also used for validation of the population assay test (see, Table 5).

In brief, the sterilized vials were tested for sterility using a filtration method. After vortexing, the contents of each vial was removed using a sterile needle and syringe, and filtered through its own filter (e.g., a 0.2 or 0.45 µm (micron) filter). Using the same needle, syringe, and filter per vial, the vials were then rinsed, vortexed, and the contents were filtered as described above. The process was then repeated to ensure all residual product was removed from each vial. After filtration of the product and vial rinsate, each filter was then rinsed and plated to tryptic soy agar (TSA). Test positive controls were performed for each organism type by rinsing a filter three times and spiking the last aliquot with 0.1 mL of the spore suspension used for inoculation. All plates were incubated according to the organism type, with *G. stearothermophilus* at 55-60° C. and *B. pumilus* at 30-35° C. for no less than 48 hours (see, Table 3).

TABLE 3

Exposed Test Samples — Sterility Testing Results

| Test Organism (Exposure (kGy)) | Test Sample (CFU) |
| --- | --- |
| B. pumilus (25-33 kGy) | 0 |
| B. pumilus (25-33 kGy) | 0 |
| B. pumilus (25-33 kGy) | 0 |
| B. pumilus (45-59 kGy) | 0 |
| B. pumilus (45-59 kGy) | 0 |
| B. pumilus (45-59 kGy) | 0 |
| G. stearothermophilus (25-33 kGy) | 0 |
| G. stearothermophilus (25-33 kGy) | 0 |
| G. stearothermophilus (25-33 kGy) | 0 |
| G. stearothermophilus (45-59 kGy) | 0 |
| G. stearothermophilus (45-59 kGy) | 0 |
| G. stearothermophilus (45-59 kGy) | 0 |
| Negative control (25-33 kGy) | 0 |
| Negative Control (45-59 kGy) | 0 |
| Positive Control | TNTC |
| Positive Control | TNTC |

Figure 2:
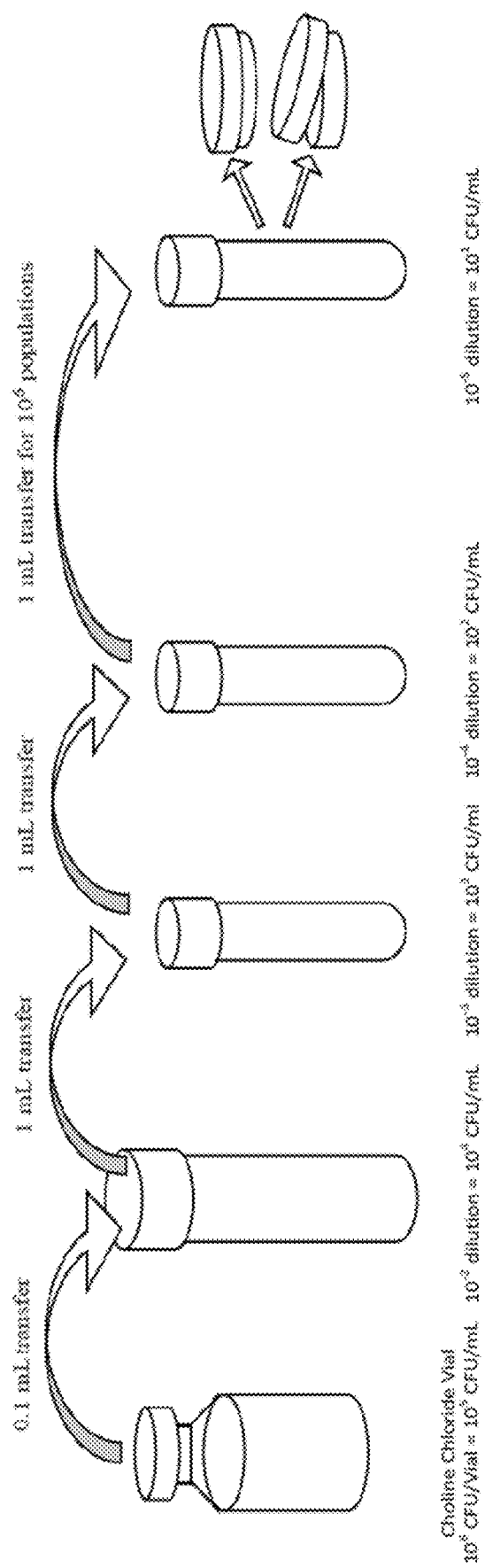
FIG. 2 depicts a serial dilution scheme as employed in Example 5.

Vials used for positive controls were tested for population and purity using a pour plate method utilizing a serial dilution scheme (see, FIG. 2). In brief, after vortexing the vial, 1 mL of each vial (i.e., vial containing choline chloride solution and either $10^5$ CFU/mL, $10^4$ CFU/mL, $10^3$ CFU/mL, or $10^2$ CFU/mL) was removed using a sterile needle and syringe, and transferre4d to a test tube containing 9 mL of sterile water. The test tube was heat shocked (e.g., 95-100° C. for 15 minutes for G. stearothermophilus and 65-75° C. for 15 minutes for B. pumilus). After heat shocking, each tube was cooled in an ice bath and vortexed. After cooling, 1 mL was transferred to a test tube containing 9 mL of sterile water and vortexed (repeated twice). These dilutions produced concentrations of $10^3$ CFU/mL, $10^2$ CFU/mL, or $10^{-1}$ CFU/mL. 1 mL from the $10^2$ and $10^1$ dilutions were plated into sterile petri dishes and 18 mL of melted TSA was poured into the petri dish and allowed to solidify. The above steps were completed for all three (3) positive control vials of each organism type. All plates were incubated according to the organism type, with G. stearothermophilus at 55-60° C. and Bacillus pumilus at 30-35° C. for no less than 48 hours. After incubation, plates were read, verified and reported for colonies as CFU/plate (see, Table 4).

TABLE 4

Population Assay for Unexposed Positive Control Vials

| Test Organism (Exposure (kGy)) | Test Sample (CFU) |
| --- | --- |
| B. pumilus ($10^1$) | 4 |
| B. pumilus ($10^1$) | 8 |
| B. pumilus ($10^1$) | 7 |
| B. pumilus ($10^2$) | 56 |
| B. pumilus ($10^2$) | 64 |
| B. pumilus ($10^2$) | 75 |
| G. stearothermophilus ($10^1$) | 2 |
| G. stearothermophilus ($10^1$) | 2 |
| G. stearothermophilus ($10^1$) | 4 |
| G. stearothermophilus ($10^2$) | 28 |
| G. stearothermophilus ($10^2$) | 25 |
| G. stearothermophilus ($10^2$) | 37 |
| Negative control | 0 |
| Negative Control | 0 |

To challenge the population assay procedure, positive controls were run. Using a sterile needle and syringe, one (1) vial of product was spiked with 0.1 mL of a G. stearothermophilus spore suspension. This inoculation resulted in a population of $10^6$ CFU in each vial. This above process was repeated using B. pumilus spore suspension. The process described above for the population assay for unexposed positive control vials was completed for both organism types. Results are documented in Table 5.

TABLE 5

Validation of Population Assay Test

| Test Organism (Exposure (kGy)) | Test Sample (CFU) |
| --- | --- |
| B. pumilus ($10^1$) | 169 |
| B. pumilus ($10^1$) | 174 |
| B. pumilus ($10^2$) | TNTC |
| B. pumilus ($10^2$) | TNTC |
| G. stearothermophilus ($10^1$) | 22 |
| G. stearothermophilus ($10^1$) | 21 |
| G. stearothermophilus ($10^2$) | 213 |
| G. stearothermophilus ($10^2$) | 183 |
| Negative control | 0 |
| Negative Control | 0 |

Vials exposed to gamma irradiation using either 25-33 kGy or 45-59 kGy showed no growth of bacteria (CFUs=0 for all samples). These data show the effectiveness of gamma irradiation as a sterilization method for choline chloride 50% (w/v) in WFI compositions. The unexposed positive control samples showed a lower population recovered than what was initially inoculated within the vials. Vials that were tested for validation of the population assay test resulted in lower CFUs than anticipated which could indicate that organisms while in solution could decrease over time with varying results/conditions. The population assay performed on test controls showed much higher recoveries than the positive control vials which indicates that the method used for inoculation was acceptable. All results indicate that, from a microbiological perspective, gamma irradiation is an effective sterilization method for choline chloride 50% (w/v) in WFI compositions against organisms such as G. stearothermophilus and B. pumilus.

II. Gamma sterilization of S. aureus

Gamma irradiation was tested as a method of sterilization for a composition of choline chloride 50% (w/v) in WFI inoculated with Staphylococcus aureus (S. aureus). Vials (5 mL) containing the composition were inoculated with 0.1 mL of an S. aureus spore suspension ($10^9$ CFU/mL). Vials were sterilized using gamma irradiation of 25-33 kGy. Select vials were left unexposed to be used as positive controls. All vials were then assayed to determine the spore populations in terms of CFUs (see, Table 7). Additional vials were also used for validation of the population assay test (see, Table 6).

Microbial retention was determined as follows. In brief, a stock solution of S. aureus was made using 10-100 CFU of organism into 15 mL of tryptic soy broth (TSB) and incubated for approximately 72 hours at 30-35° C., creating a culture of approximately $10^9$ CFU/mL (approximated using a number 4 McFarland Standard). A dilutions series of the stock culture was made in duplicate to test for population verification by plating $10^3$ and $10^2$ dilutions in duplicate to TSA and incubated at 30-35° C. for no more than 24 hours. 5 mL product vials were spiked with 0.1 mL of the prepared stock culture. Serial dilutions of the spiked product vials were also made in duplicate using 0.1 mL of the spiked product into 9.9 mL of sterile water, then 1 mL of that dilution into 9 mL of sterile water. Both dilutions were plated in duplicate using 0.1 mL to TSA and incubated at 30-35° C. for no more than 24 hours. Serial dilutions of the same spiked product vials were tested as above in time increments of 24 hours, 72 hours, and 7 days. Microbial retention results can be seen in Table 6.

TABLE 6

Microbial Retention Results

| Sample | 1st Dilution (10³) CFU | 2nd Dilution (10²) CFU |
|---|---|---|
| Stock Culture (T:0hr) | TNTC/TNTC | 300/100 |
| Product Dilution (T:0hr) | TNTC/TNTC | 430/480 |
| Product Dilution (T:24hr) | TNTC/TNTC | 430/440 |
| Product Dilution (T:72hr) | TNTC/TNTC | 490/550 |
| Product Dilution (T:7day) | TNTC/TNTC | 255/266 |

Sterility results for *S. aureus* were obtained as follows. A stock culture of *Staphylococcus aureus* was made using 10-100 CFU of organism into 15 mL of TSB and incubated for approximately 72 hours in 30-35° C., creating a culture of approximately $10^9$ CFU/mL (approximated using a number 4 McFarland Standard). A dilution series of the stock culture was made in duplicate to test for population verification by plating $10^3$ and $10^2$ dilutions in duplicate to TSA and incubated at 30-35° C. for no more than 24 hours. Three 5 mL product vials were spiked with 0.1 mL of the prepared stock culture. Two additional product vials were spiked with 0.1 mL of the stock culture to serve as positive controls. Two vials remained without inoculation to serve as negative controls. These vials were sterilized using gamma irradiation of 25-33 kGy (positive and negative controls remained unexposed). Post sterilization, the three exposed vials as well as the negative controls were tested using a filtration method. The contents of each vial were separately filtered through a 0.45 μm MCE filter. The vial was rinsed and filtered along with the remaining rinsate in three approximate 100 mL aliquots. The filter was plated to TSA and incubated at 30-35° C. for 5 days. Serial dilutions of the spiked product vials used for positive controls were made in duplicate using 0.1 mL of the spiked product into 9.9 mL of sterile water, then 1 mL of that dilution into 9 mL of sterile water, which was repeated three times. The final 3 dilutions were plated in duplicate using 0.1 mL to TSA and incubated at 30-35° C. for 5 days. Sterility results for *S. aureus* are shown in Table 7.

TABLE 7

Determination of Sterility Results *S. aureus*

| Test Organism (Exposure (kGy)) | Test Sample (CFU) |
|---|---|
| Stock Culture 1st (10^3) Dilution | TNTC/TNTC |
| Stock Culture 2nd (10^2) Dilution | 132/108 |
| Positive Control 1 - 10^2 | 0/0 |
| Positive Control 2 - 10^2 | 0/0 |
| Positive Control 1 - 10^3 | 0/1 |
| Positive Control 2 - 10^3 | 0/2 |
| Positive Control 1 - 10^4 | 207/238 |
| Positive Control 2 - 10^4 | 292/182 |
| Negative Control 1 | 0 |
| Negative Control 2 | 0 |
| Product Vial 1 | 0 |
| Product Vial 2 | 0 |
| Product Vial 3 | 0 |

The population verifications for both stock culture inoculums used for the microbial retention and determination of sterility studies confirm the correct reported populations. Inoculated product vials were able to show microbial retention over an extended period of time with minimal decrease in population. The microbial retention study showed a zero log reduction over a weeks' time, whereas the positive controls tested from the determination of sterility study showed a two-three log reduction over >5 weeks between inoculation and testing. The terminal sterilization utilizing gamma irradiation is proven effective by results of 0 CFU recoveries in all three exposed product vials. The results indicate that, from a microbiological perspective, gamma irradiation is an effective sterilization method for choline chloride 50% (w/v) in WFI compositions against organisms such as *S. aureus*. The combination of high ionic strength and gamma irradiation has been shown to be very effective for sterilization of choline chloride aqueous compositions.

Example 6

Forced Degradation of Choline Chloride

Choline chloride was exposed to stress conditions as shown in Table 8.

TABLE 8

Treatments for Forced Degradation Study

| Treatment | Conditions |
|---|---|
| Control | No treatment |
| Acid 1 | 1 N HCl for about 72 hours, ambient |
| Acid 2 | 0.1 N HCl for about 72 hours, ambient |
| Base 1 | 1 N NaOH for about 72 hours, ambient |
| Base 2 | 0.1 N NaOH for about 72 hours, ambient |
| Oxidation | 5% $H_2O_2$ for about 24 hours, ambient |
| Light, dry | Stored in Alcami Light Bank 3, or equivalent (about 7.2 kilolux) Visible and 1 W/m²UV) for about 120 hours |
| Light, wet | In the presence of water Stored in Alcami Light Bank 3, or equivalent (about 7.2 kilolux) Visible and 1 W/m²UV) for about 120 hours |
| Heat, dry | 80° for about 72 hours |
| Heat, wet | In the presence of water 80° for about 72 hours |

Each forced degradation solution was prepared by transferring 25 mg of the choline chloride into a 100 mL volumetric flask followed by exposure to the appropriate condition. At the end of the treatment, the acid and base treated samples were neutralized with an equivalent amount of hydrochloric acid or sodium hydroxide. After equilibration to room temperature, each degradation sample was prepared according to the test method. The treated sample preparations along with the control were analyzed (single injection) according to the method, except the run time was extended to allow for potential late-eluting degradation peaks. Mass balance was examined for each treatment.

The results of the forced degradation study are shown in Table 9. The method was capable of separating known (trimethylamine) and unknown degradation products in the presence of acid, base, oxidation, light, and heat to the extent that they could accurately be quantified. Two unknown impurities were observed in the oxidation stressed samples (RRT 0.75 and 0.78 at approximately 0.3% each) and one unknown (RRT 1.42/1.44 at 0.14%) was observed in the acid and base stressed sample. Chromatographic resolution between the active and the closest-eluting peak (if present at a level of ≥0.05%) was not less than (NLT) 1.2 and degradation peaks ≥0.05% were resolved from each other and from choline chloride to the extent that they could be quantified (target resolution NLT 1.2). Additionally, the chromatography showed acceptable mass balance for all stressed conditions. Choline chloride showed good stability at all stressed conditions, where no significant degradation was observed when exposed to the maximum stress conditions. As such, no significant degradation of choline chloride is expected under the conditions of sterilization via gamma irradiation as described in Example 5.

TABLE 9

| | | | | | | | | | | | |
|---|---|---|---|---|---|---|---|---|---|---|---|
| Result | Description | Control | Acid 1 | Acid 2 | Base 1 | Base 2 | Oxidation | Heat (dry) | Heat (wet) | Light (dry) | Light (wet) |
| Assay | % LC | 98.7 | 99.1 | 98.9 | 99.3 | 100.8 | 99.4 | 99.2 | 99.4 | 99.7 | 98.9 |
| | % Relative to control | — | 100.4 | 100.2 | 100.6 | 102.1 | 100.7 | 100.5 | 100.7 | 101.0 | 100.2 |
| % Impurities | Trimethylamine | — | — | — | — | — | — | — | — | — | — |
| | RRT 0.75 | — | — | — | — | — | 0.28 | — | — | — | — |
| | RRT 0.78 | — | — | — | — | — | 0.27 | — | — | — | — |
| | RRT 1.42/1.44 | — | 0.14 | — | 0.14 | — | — | — | — | — | — |
| | Total Impurities | — | 0.14 | — | 0.14 | — | 0.55 | — | — | — | — |
| Mass Balance | Assay + Impurities | 98.7 | 99.24 | 98.9 | 99.44 | 100.8 | 99.95 | 99.2 | 99.4 | 99.7 | 98.9 |
| | % Relative to Control | — | 100.5 | 100.2 | 100.7 | 102.1 | 101.3 | 100.5 | 100.7 | 101.0 | 100.2 |
| Resolution | Choline Chloride | — | 4.5 | 4.6 | 3.6 | 4.6 | 3.2 | 7.8 | 7.8 | 7.9 | 7.9 |
| | Trimethylamine | — | — | — | — | — | — | — | — | — | — |

Example 7

Stability of Choline Salt Compositions

Choline Chloride Solution 50% (w/v) in WFI was prepared and transferred to either Type I glass tubular vials or delamination controlled (DC) vials and stored for 6 months under either 25° C./60% relative humidity (RH) or 40° C./75% RH storage conditions to evaluate stability. Data for the 3 month stability results are summarized in Tables 10-13. The results indicate acceptable stability of the drug product at both the storage conditions, viz. 25° C./60% RH and 40° C./75% RH.

TABLE 10

Stability Data Type I glass tubular vials at 25° C./60% RH

| Sample | Acceptance Criteria | 0 month | 1 month | 2 month | 3 month |
|---|---|---|---|---|---|
| Visual Appearance | Clear, colorless solution free of visible particulates | Conforms | Conforms | Conforms | Conforms |
| pH | Report Results | 5.7 | 6.2 | 6.2 | 6.2 |
| Assay % LC | 90.0%-110.0% LC | 98.1 | 99.5 | 99.4 | 99.5 |
| Related Substance (% Total impurities) | Report Results % Trimethylamine | <0.05 | <0.05 | <0.05 | <0.05 |
| | Unknown Impurities (RRT/%) | <0.05 | Not reported | Not reported | Not reported |
| | % Total Impurities | <0.05 | <0.05 | <0.05 | <0.05 |
| Particulate matter (HIAC) | particles ≥ 10 μm | 10 | Not Scheduled | Not Scheduled | 2 |
| | particles ≥ 25 μm | 0 | Not Scheduled | Not Scheduled | 0 |
| Osmolality | Report results (mOsm/kg) | *645 | Not Scheduled | Not Scheduled | Not Scheduled |

TABLE 11

Stability Data Type I glass tubular vials at 40° C./75% RH

| Sample | Acceptance Criteria | 0 month | 1 month | 2 month | 3 month |
|---|---|---|---|---|---|
| Visual Appearance | Clear, colorless solution free of visible particulates | Conforms | Conforms | Conforms | Conforms |
| pH | Report Results | 5.7 | 6.2 | 6.0 | 6.8 |
| Assay % LC | 90.0%-110.0% LC | 98.1 | 99.7 | 99.5 | 99.6 |
| Related Substance (% Total impurities) | Report Results % Trimethylamine | <0.05 | <0.05 | <0.05 | <0.05 |
| | Unknown Impurities (RRT/%) | <0.05 | Not reported | Not reported | Not reported |
| | % Total Impurities | <0.05 | <0.05 | <0.05 | <0.05 |

TABLE 11-continued

Stability Data Type I glass tubular vials at 40° C./75% RH

| Sample | Acceptance Criteria | 0 month | 1 month | 2 month | 3 month |
|---|---|---|---|---|---|
| Particulate matter (HIAC) | particles ≥ 10 μm | 10 | Not Scheduled | Not Scheduled | 1 |
| | particles ≥ 25 μm | 0 | | | 0 |
| Osmolality | Report results (mOsm/kg) | *645 | Not Scheduled | Not Scheduled | Not Scheduled |

TABLE 12

Stability Data DC vials at 25 C./60% RH

| Sample | Acceptance Criteria | 0 month | 1 month | 2 month | 3 month |
|---|---|---|---|---|---|
| Visual Appearance | Clear, colorless solution free of visible particulates | Conforms | Conforms | Conforms | Conforms |
| pH | Report Results | 5.7 | 6.2 | 6.3 | 6.5 |
| Assay % LC | 90.0%-110.0% LC | 98.9 | 99.5 | 99.4 | 99.9 |
| Related Substance (% Total impurities) | Report Results % Trimethylamine | <0.05 | <0.05 | <0.05 | <0.05 |
| | Unknown Impurities (RRT/%) | <0.05 | Not reported | Not reported | Not reported |
| | % Total Impurities | <0.05 | <0.05 | <0.05 | <0.05 |
| Particulate matter (HIAC) | particles ≥ 10 μm | 5 | Not Scheduled | Not Scheduled | 2 |
| | particles ≥ 25 μm | 0 | | | <1 |
| Osmolality | Report results (mOsm/kg) | *637 | Not Scheduled | Not Scheduled | Not Scheduled |

TABLE 13

Stability Data DC vials at 40° C./75% RH

| Sample | Acceptance Criteria | 0 month | 1 month | 2 month | 3 month |
|---|---|---|---|---|---|
| Visual Appearance | Clear, colorless solution free of visible particulates | Conforms | Conforms | Conforms | Conforms |
| pH | Report Results | 5.7 | 6.2 | 6.2 | 6.9 |
| Assay % LC | 90.0%-110.0% LC | 98.9 | 99.7 | 99.6 | 99.4 |
| Related Substance (% Total impurities) | Report Results % Trimethylamine | <0.05 | <0.05 | <0.05 | <0.05 |
| | Unknown Impurities (RRT/%) | <0.05 | Not reported | Not reported | Not reported |
| | % Total Impurities | <0.05 | <0.05 | <0.05 | <0.05 |
| Particulate matter (HIAC) | particles ≥ 10 μm | 5 | Not Scheduled | Not Scheduled | 3 |
| | particles ≥ 25 μm | 0 | | | 0 |
| Osmolality | Report results (mOsm/kg) | *637 | Not Scheduled | Not Scheduled | Not Scheduled |

Example 8 pH Study of Choline Salt Compositions

Figure 3:
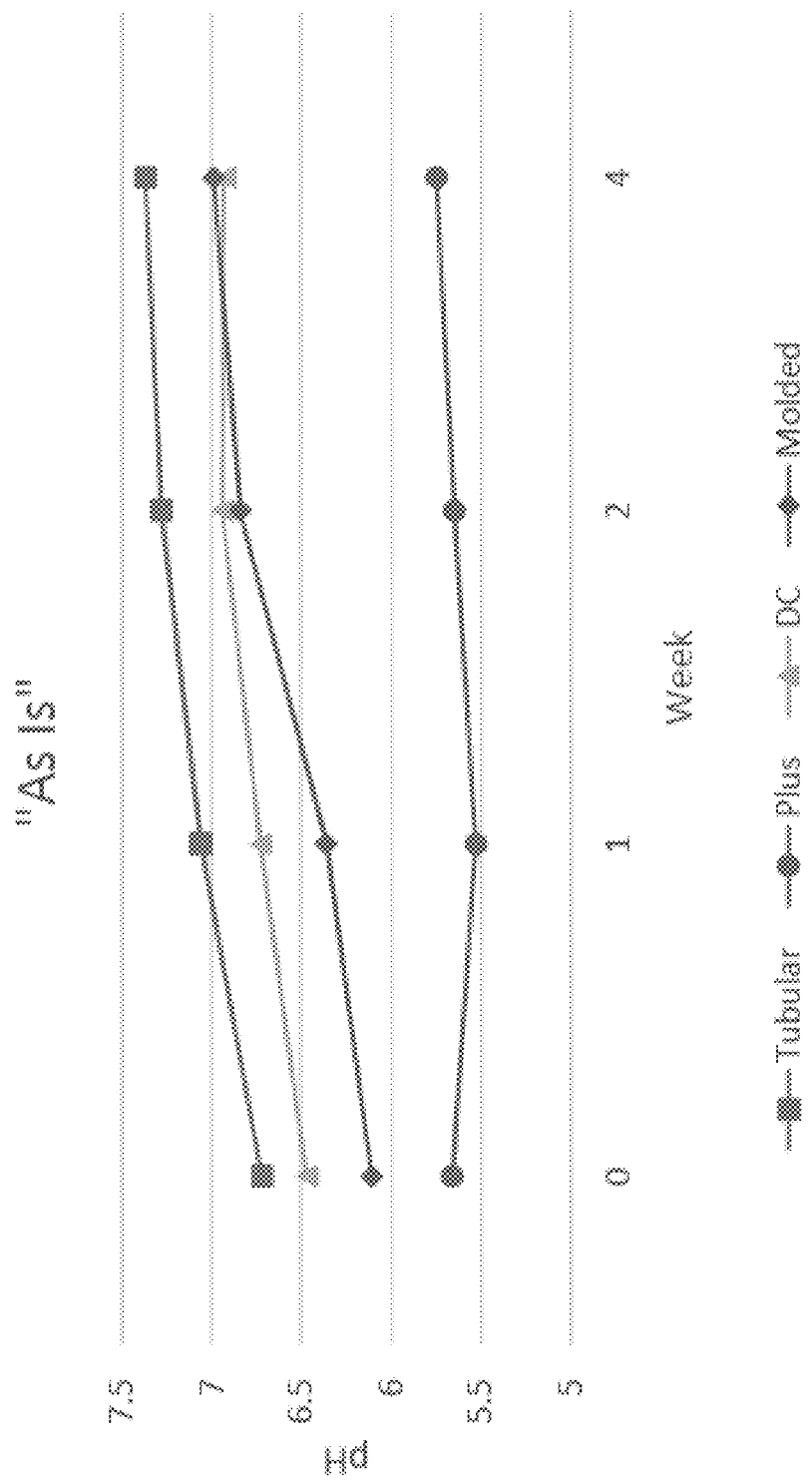
FIG. 3 plots the pH results for "As is" samples of a pH study of choline chloride solution 50% w/v in water for injection (WFI) before and after terminal sterilization by heat.
Figure 4:
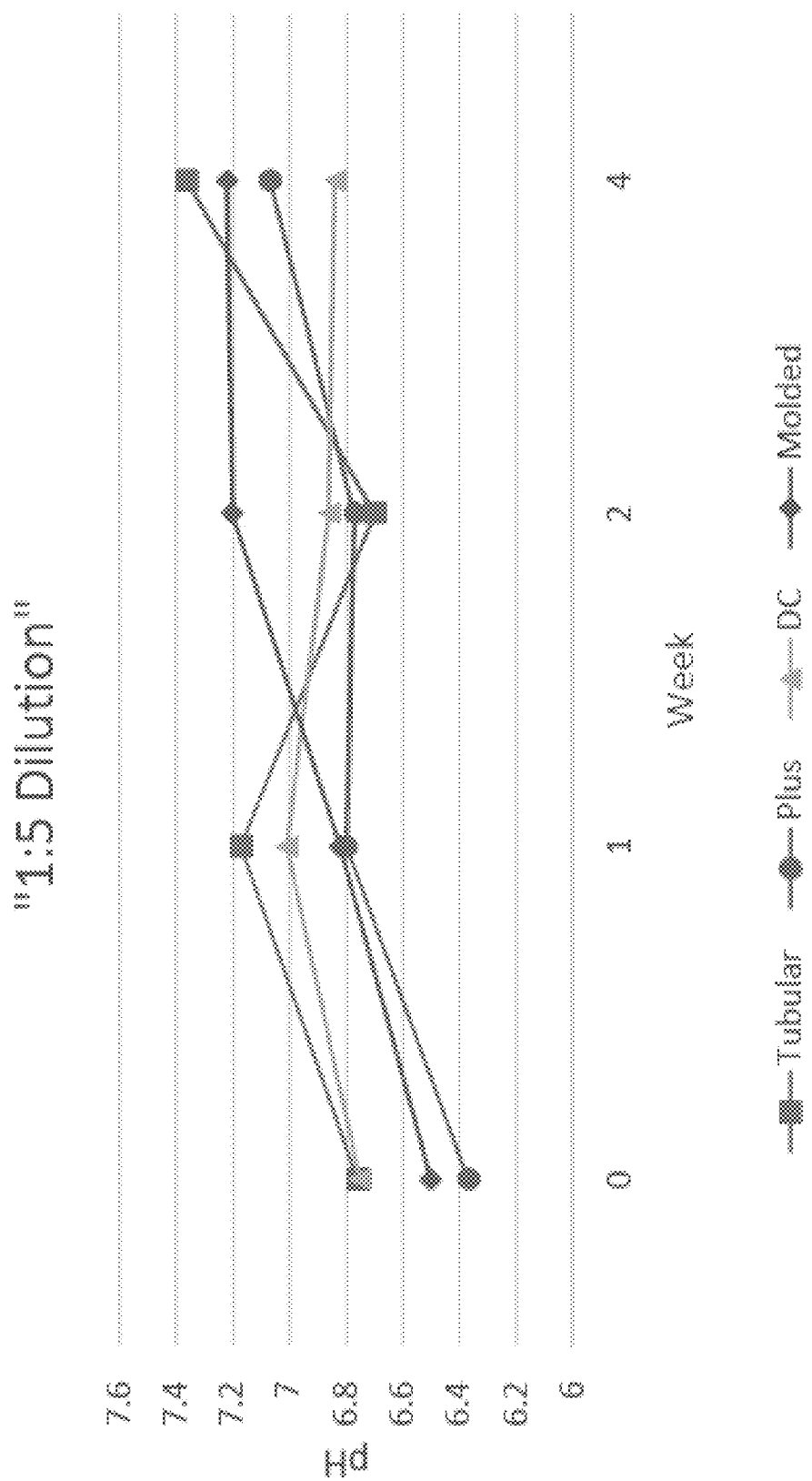
FIG. 4 plots the pH results for "1:5 dilution" samples of a pH study of choline chloride solution 50% w/v in WFI before and after terminal sterilization by heat.

A pH study was conducted to evaluate the pH of Choline Chloride solution after terminal sterilization with heat. Choline chloride solution 50% w/v in WFI was prepared according to Example 1. Several vial types were also evaluated including Schott Type I glass tubular vials, Schott Type I plus glass vials, Schott Delamination Controlled (DC) glass vials and Kimble Type I glass molded vials. In brief, choline chloride solution 50% w/v in WFI (5.5 mL) was filled in each type of vial. Two filled vials of each type were retained as controls and the rest of the vials were terminally sterilized at 121° C. for 45 minutes. 10% Choline chloride active pharmaceutical ingredient (API) in water is the recommended USP method to determine the pH of choline chloride API. Therefore, 1:5 dilution of 50% choline chloride in WFI solution was also included in the pH study at each time point. At each time point, contents from 2 vials of each vial type were pooled together respectively. 2 mL of the pooled solution was diluted with 8 mL WFI to prepare 1:5 dilution samples. The remaining 9 mL solution was tested for "as is" (no dilution) samples. For Before TS (Terminal Sterilization) samples, 2 retained vials from each vial type were kept at room temperature until the terminal sterilized samples were ready to be tested. All the pH checks were performed then at the same time. At each time point, pH meter was calibrated with 4.0, 7.0 and 10.0 pH standards, and then the pH of samples were tested (see, Table 14). For each type of vial, pH change over time is plotted in FIG. 3 and FIG. 4. FIG. 3 plots the pH results for "As is" samples and FIG. 4 plots the pH results for "1:5 dilution" of choline chloride solution 50% w/v in WFI before and after terminal sterilization by heat.

salt compositions as described in Examples 1-7 may also be used for the treatment of choline deficiency in a subject related to Intestinal Failure Associated Liver Disease (IF-ALD), fatty liver disease (e.g., alcoholic fatty liver (AFL), alcoholic steatohepatitis (ASH), non-alcoholic fatty liver (NAFL), non-alcoholic steatohepatitis (NASH), NASH-associated liver fibrosis, or ASH-associated liver fibrosis). Choline salt compositions as described in Examples 1-7 may be used as a component of parenteral support. Choline salt compositions as described in Examples 1-7 may also be used as a component of parenteral nutrition.

TABLE 14 pH Study Results

| | | | | | | | | | | | |
|---|---|---|---|---|---|---|---|---|---|---|---|
| | Bulk Solution | | Initial | | | | | | T = 2 week | | T = 4 week | |
| | | | Before TS* | | After TS* | | T = 1 week | | (If required) | | (If required) | |
| Vials | "as is" | 1:5 dilution | "as is" | 1:5 dilution | "as is" | 1:5 dilution | "as is" | 1:5 dilution | "as is" | 1:5 dilution | "as is" | 1:5 dilution |
| Type I glass tubular vials (control) | 5.7 | 6.7 | 6.2 | 6.6 | 6.7 | 6.8 | 7.1 | 7.2 | 7.3 | 6.7 | 7.4 | 7.4 |
| Type I plus glass vials | | | 5.5 | 6.4 | 5.7 | 6.4 | 5.5 | 6.8 | 5.7 | 6.8 | 5.8 | 7.1 |
| DC glass vials | | | 5.9 | 6.6 | 6.5 | 6.8 | 6.7 | 7.0 | 6.9 | 6.9 | 6.9 | 6.8 |
| Type I glass molded vials | | | 5.9 | 6.6 | 6.1 | 6.5 | 6.4 | 6.8 | 6.8 | 7.2 | 7.0 | 7.2 |

Results show that the pH of the solution drifted upwards during the course of this study. As compared to the initial pH reading, solution pH in Type I plus vial did not drift as much and was stable for measuring pH for samples "as is" without dilution. Type I tubular vials, DC and Molded vials showed an initial pH drift upwards and then flattened at the 4 week time point. As compared to "As is" pH results, 1:5 dilution results were higher for Type I Plus and Molded vials, and comparable for Type I Tubular and DC vials respectively. pH results for 1:5 dilution for DC vials were stable as compared to other vial types.

Example 9

Methods of Treatment with Choline Salt Compositions

Choline salt compositions as described in Examples 1-7 may be used for the treatment of choline deficiency in a subject related to liver steatosis and/or cholestasis. Choline Example 10

Synthesis of Choline Chloride

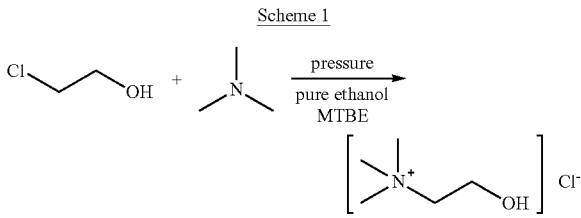

Scheme 1

Choline chloride was synthesized by combining gaseous trimethylamine in a hydrogenator under pressure with 2-chloroethanol in the presence of ethanol and methyl-tertiary-butyl ether.

Example 11

Analysis of Choline Chloride

Choline chloride as synthesized in Example 10 was subjected to analysis. The results for two different batches of choline chloride are found in Table 15. Both batches were analyzed three months post production.

TABLE 15

| Test | Specification | Batch 1 Results | Batch 2 Results |
| --- | --- | --- | --- |
| Appearance | white to off-white solid | Off-white solid | White solid |
| ID by FTIR | The IR absorption spectrum of the preparation of the test specimen exhibits maxima only at the same wavelengths as that of a similar preparation of the corresponding USP reference standard | IR absorption spectrum of the preparation of the test specimen exhibits maxima only at the same wavelengths as that of a similar preparation of the corresponding USP reference standard | IR absorption spectrum of the preparation of the test specimen exhibits maxima only at the same wavelengths as that of a similar preparation of the corresponding USP reference standard |
| ID by RT | The retention time of the choline chloride in the sample solution must be within ±02.0% of the average retention time of choline chloride in the bracketing standard solution | RT of choline chloride sample solution is within ±02.0% average RT of choline chloride in bracketing standard solution | RT of choline chloride sample solution is within ±02.0% average RT of choline chloride in bracketing standard solution |
| Water Content by KF | NMT 0.5% | 0.2% (0.23%) | <0.1% |
| (<0.05%)Residue on Ignition | NMT 0.05% | 0.01% | 0.00% |
| pH (1 in 10 solution) | Between 4.0-7.0 in solution | Not Determined | 5.9 |
| Assay by HPLC | 99.0-100.5% on the anhydrous basis | 99.5% | 99.8% |
| Total Impurities by HPLC | Total ≤2.0% | <0.05% | <0.1%(<0.05%) |
| Specified Impurities by HPLC | Individual Specified ≤0.3% | <0.05% | <0.1%(<0.05%) |
| | Individual Unknown ≤0.10% | None Detected | None Detected |
| Chloride Counter Ion Content by IC | 24.1-26.7% w/w | 25.5% | 25.1% |
| Residual Solvents by GC-MS | Ethanol - NMT 5000 ppm | <QL | 778 ppm |
| | MTBE - NMT 5000 ppm | <QL | <QL |
| Residual Chloroethanol by GC-MS | NMT 0.75 ppm | <QL | < QL(0.19 ppm) |
| Elemental Impurities by ICP-MS | Element / Limit (ug/g) | Limit (ug/g) | Limit (ug/g) |
| | Cd  0.2 | <0.05 | <0.05 |
| | Pb  0.5 | <0.125 | <0.125 |
| | As  1.5 | <0.375 | <0.375 |
| | Hg  0.3 | <0.075 | <0.075 |
| | Co  0.5 | <0.125 | <0.125 |
| | V   1 | <0.25 | <0.25 |
| | Ni  2 | <0.5 | <0.5 |
| | Li  25 | <6.25 | <6.25 |
| | Sb  9 | <2.25 | <2.25 |
| | Cu  30 | <7.5 | <7.5 |
| | Al  0.2 | 0.05 | <0.05 |
| Bacterial Endotoxins | NMT 5.7 EU/mg | <0.1 EU/mg | <0.1 EU/mg |
| Microbial Enumeration | Total Aerobic Microbial Count (TAMC) - NMT 1000 CFU/g | <10 CFU/g | <10 CFU/g |
| | Total Yeast and Mold Count (TYMC) - NMT 100 CFU/g | <10 CFU/g | <10 CFU/g |

Results of the choline chloride analysis show that both batches were produced in high purity (99.5% and 99.8%, respectively). The amount of residual chloroethanol was below the quantitation limit (QL). Additionally, the amount of aluminum found was ≤0.05 ug/g of choline chloride.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sterile composition for intravenous injection, comprising choline chloride in an aqueous medium, wherein the choline chloride is present in the composition at a level of 25-75% choline chloride by weight/volume %, and wherein the composition:
   has been sterilized by gamma irradiation at a dose of at least 20 kGy;
   has a sterility assurance level of at least $10^{-6}$;
   contains less than $10^{-1}$ CFU/mL of *S. aureus, G. stearothermophilus*, and/or *B. pumilus;*
   does not contain a preservative;
   contains a preservative;
   contains at least one amino acid, at least one vitamin, and/or at least one fatty acid;
   has an ionic strength of 0.3-7 Molar;
   has an ionic strength of about 7 Molar; or
   has a pH of about 4-7.

2. The sterile composition of claim 1, wherein the composition contains 50% choline chloride by weight/volume %.

3. The sterile composition of claim 1, wherein the aqueous medium is water for injection.

4. The sterile composition of claim 1, wherein the composition has been sterilized by gamma irradiation at a dose of at least 20 kGy.

5. The sterile composition of claim 4, wherein the composition has been sterilized by gamma irradiation at a dose of 25-33 kGy.

6. The sterile composition of claim 1, wherein the composition has a sterility assurance level of at least $10^{-6}$.

7. The sterile composition of claim 1, wherein the composition contains less than $10^{-1}$ CFU/mL of *S. aureus, G. stearothermophilus*, and/or *B. pumilus*.

8. The sterile composition of claim 1, wherein the composition does not contain a preservative.

9. The sterile composition of claim 1, wherein the composition contains a preservative.

10. The sterile composition of claim 1, wherein the composition contains at least one amino acid, at least one vitamin, and/or at least one fatty acid.

11. The sterile composition of claim 1, wherein the composition contains a pharmaceutically acceptable carrier, diluent, or excipient.

12. The sterile composition of claim 1, wherein the composition has an ionic strength of 0.3-7 Molar.

13. The sterile composition of claim 1, wherein the composition has an ionic strength of about 7 Molar.

14. The sterile composition of claim 1, wherein the composition has a pH of about 4-7.

15. The sterile composition of claim 1, wherein the composition is suitable for administration via indirect injection or via direct injection.

16. A sterile composition for intravenous injection, comprising choline chloride in an aqueous medium, wherein the choline chloride is present in the composition at a level of 25-75% choline chloride by weight/volume %, and wherein the composition has been sterilized by gamma irradiation at a dose of at least 20 kGy.

17. The sterile composition of claim 16, wherein the composition contains 50% choline chloride by weight/volume %.

18. The sterile composition of claim 16, wherein the composition has been sterilized by gamma irradiation at a dose of 25-33 kGy.

19. The sterile composition of claim 16, wherein the composition has a sterility assurance level of at least 10'.

20. The sterile composition of claim 16, wherein the composition contains less than $10^1$ CFU/mL of *S. aureus, G. stearothermophilus* and/or *B. pumilus*.

* * * * *

UNITED STATES PATENT AND TRADEMARK OFFICE
CERTIFICATE OF CORRECTION

| | | |
|---|---|---|
| PATENT NO. | : 11,311,503 B1 | Page 1 of 1 |
| APPLICATION NO. | : 17/246438 | |
| DATED | : April 26, 2022 | |
| INVENTOR(S) | : Dayton Reardan et al. | |

It is certified that error appears in the above-identified patent and that said Letters Patent is hereby corrected as shown below:

In the Claims

<u>Column 35, Claim 1, Lines 34-35:</u>
"stearothermophilus, and/or B." should read: --stearothermophilus and/or B.--

<u>Column 36, Claim 19, Line 43:</u>
"at least 10'." should read: --at last $10^{-6}$.--

<u>Column 36, Claim 20, Line 45:</u>
"than $10^1$" should be: --than $10^{-1}$--

Signed and Sealed this
Twelfth Day of December, 2023

Katherine Kelly Vidal
*Director of the United States Patent and Trademark Office*